US010058100B2

(12) United States Patent
Wood et al.

(10) Patent No.: US 10,058,100 B2
(45) Date of Patent: Aug. 28, 2018

(54) HYDROGEN SULFIDE RELEASING COMPOUNDS AND THEIR USE

(71) Applicant: THE UNIVERSITY OF EXETER, Devon (GB)

(72) Inventors: Mark Wood, Devon (GB); Matthew Whiteman, Devon (GB); Alexis Perry, Devon (GB)

(73) Assignee: The University of Exeter, Exeter, Devon (GB)

( * ) Notice: Subject to any disclaimer, the term of this patent is extended or adjusted under 35 U.S.C. 154(b) by 220 days.

(21) Appl. No.: 14/347,782

(22) PCT Filed: Oct. 1, 2012

(86) PCT No.: PCT/GB2012/052424
§ 371 (c)(1),
(2) Date: Mar. 27, 2014

(87) PCT Pub. No.: WO2013/045951
PCT Pub. Date: Apr. 4, 2013

(65) Prior Publication Data
US 2015/0196034 A1 Jul. 16, 2015

(30) Foreign Application Priority Data

Sep. 30, 2011 (GB) .................. 1117095.8

(51) Int. Cl.
A01N 57/24 (2006.01)
C07F 9/54 (2006.01)
C07F 9/6553 (2006.01)
A61K 31/662 (2006.01)
A61K 47/48 (2006.01)
A61K 31/385 (2006.01)

(52) U.S. Cl.
CPC ............ A01N 57/24 (2013.01); A61K 31/385 (2013.01); A61K 31/662 (2013.01); A61K 47/48023 (2013.01); C07F 9/5442 (2013.01); C07F 9/655345 (2013.01)

(58) Field of Classification Search
None
See application file for complete search history.

(56) References Cited

U.S. PATENT DOCUMENTS

2004/0053989 A1* 3/2004 Prendergast ......... A61K 31/385
514/440
2008/0004245 A1 1/2008 Wallace et al.
2010/0273743 A1 10/2010 Moore et al.

FOREIGN PATENT DOCUMENTS

| CA | 2 354 743 A1 | 2/2003 |
| WO | 2006/113914 A2 | 10/2006 |
| WO | 2007/046729 A1 | 4/2007 |
| WO | 2008/146105 A1 | 12/2008 |
| WO | 2009/012534 A1 | 1/2009 |
| WO | 2009/065926 A2 | 5/2009 |
| WO | 2010/110684 A1 | 9/2010 |
| WO | 2013/045951 A1 | 4/2013 |
| WO | 2015/185918 A1 | 12/2015 |

OTHER PUBLICATIONS

Szczesny et al. NIH Public Access, Author Manuscript, Nitric Oxide (2014), pp. 1-27.*
STN online, file HCAPLUS, Acc. No. 1962:73569, Doc. No. 56:73569 (Rauhut et al., Journal of Organic Chemistry (1961), vol. 26, pp. 5135-5138), Abstract.*
Ahmad et al., "AP39, A Mitochondrially Targeted Hydrogen Sulfide Donor, Exerts Protective Effects in Renal Epithelial Cells Subjected to Oxidative Stress in vitro and in Acute Renal Injury in vivo," SHOCK, 2016, pp. 88-97, vol. 45, No. 1.
Ahmad et al., "Both the H2S biosynthesis inhibitor aminooxyacetic acid and the mitochondrially targeted H2S donor AP39 exert protective effects in a mouse model of burn injury," Pharmacological Research, 2016, pp. 348-355, vol. 113.
Chatzianastasiou et al., "Cardioprotection by H2S Donors: Nitric Oxide-Dependent and -Independent Mechanisms," The Journal of Pharmacology and Experimental Therapeutics, 2016, pp. 431-440, vol. 358.
Gero et al., "The novel mitochondria-targeted hydrogen sulfide (H2S) donors AP123 and AP 39 protect against hyperglycemic injury in microvascular endothelial cells in vitro," Pharmacological Research, 2016, pp. 186-198, vol. 113.
Ikeda et al., "Mitochondria-targeted hydrogen sulfide donor AP39 improves neurological outcomes after cardiac arrest in mice," Nitric Oxide, 2015, pp. 90-96, vol. 49.
Kimura et al., "Hydrogen sulfide increases glutathione production and suppresses oxidative stress in mitochondria," J. Pharmacol. Sci., 2010, 112 (Suppl. 1), p. 88P, Abstract No. OIE-1-3.
Le Trionnaire et al., "The synthesis and functional evaluation of a mitochondria-targeted hydrogen sulfide donor, (10-oxo-10-(4-(3-thioxo-3H-1,2-dithiol-5-yl)-phenoxy)decyl)triphenylphosphonium bromide (AP39)," Med. Chem. Commun., 2014, pp. 728-736, vol. 5.
Lobb et al., "Hydrogen Sulfide Protects Renal Grafts Against Prolonged Cold Ischemia-Reperfusion Injury via Specific Mitochondrial Actions," American Journal of Transplantation, 2016, pp. 1-12.
Minamishima et al., "Emerging Role of Hydrogen Sulfide in Organ Protection and Survival," ICU & CCU, 2009, pp. 993-1000, vol. 33, No. 12, with partial English Translation.
Reynolds, "Potential Relevance of Bell-Shaped and U-Shaped Dose-Responses for the Therapeutic Targeting of Angiogenesis in Cancer," Dose-Response, 2010, pp. 253-284, vol. 8.

(Continued)

Primary Examiner — Hasan Syed Ahmed
Assistant Examiner — Frank Choi

(57) ABSTRACT

The invention relates to a compound comprising a mitochondrial targeting group linked to group capable of releasing hydrogen sulfide, or a pharmaceutically acceptable salt thereof, for use in the treatment of the human or animal body by surgery or therapy. The invention also relates to the use of the compound in the treatment of a plant, and to certain forms of the compound.

6 Claims, 29 Drawing Sheets

(56) References Cited

OTHER PUBLICATIONS

Schiller et al., "Synthesis and in vitro opioid activity profiles of DALDA analogues," European Journal of Medicinal Chemistry, 2000, pp. 895-901, vol. 35, No. 10.

Tomasova et al., "Effects of AP39, a novel triphenylphosphonium derivatised anethole dithiolethione hydrogen sulfide donor, on rat haemodynamic parameters and chloride and calcium Cav3 and RyR2 channels," Nitric Oxide, 2015, pp. 131-144, vol. 46.

Wang et al., "The use of mitochondrial targeting resveratrol liposomes modified with a dequalinium polyethylene glycol-distearoylphosphatidyl ethanolamine conjugate to induce apoptosis in resistant lung cancer cells," Biomaterials, 2011, pp. 5673-5687, vol. 32, No. 24.

Yamada et al., "MITO-Porter: A liposome-based carrier system for delivery of macromolecules into mitochondria via membrane fusion," Biochimica et Biophysica Acta, 2008, pp. 423-432, vol. 1778, No. 2.

Zhao et al., "AP39, a Mitochondria-Targeted Hydrogen Sulfide Donor, Supports Cellular Bioenergetics and Protects against Alzheimer's Disease by Preserving Mitochondrial Function in APP/PS1 Mice and Neurons," Oxidative Medicine and Cellular Longevity, 19 pgs., vol. 2016, Article ID 8360738.

Arner et al., "1-Chloro-2,4-dinitrobenzene Is an Irreversible Inhibitor of Human Thioredoxin Reductase: Loss of Thioredoxin Disulfide Reductase Activity Is Accompanied by a Large Increase in NADPH Oxidase Activity", The Journal of Biological Chemistry, 1995, pp. 3479-3482, vol. 270, No. 8.

Busch et al., "Diallylpolysulfides induce growth arrest and apoptosis", International Journal of Oncology, 2010, pp. 743-749, vol. 36.

Cai et al., "Small molecule inhibitors of mammalian thioredoxin reductase", Free Radical Biology & Medicine, 2012, pp. 257-265, vol. 52, No. 2.

Cortese-Krott et al., "Nitrosopersulfide (SSNO—) accounts for sustained NO bioactivity of S-nitrosothiols following reaction with sulfide", Redox Biology, 2014, pp. 234-244, vol. 2.

Ferguson et al., "Potentiation of Methyl Aminolevulinate (MAL)-Induced Photodynamic Therapy (PDT) Killing of Skin Cancer Cells by Mitochondria-Targeted Hydrogen Sulfide (H2S) Donors", Free Radical Biology & Medicine, 2014, p. S135, vol. 76.

Finkelstein et al., "Auranofin. New oral gold compound for treatment of rheumatoid arthritis", Annals of the Rheumatic Diseases, 1976, pp. 251-257, vol. 35.

Gromer et al., "Human Placenta Thioredoxin Reductase: Isolation of the Selenoenzyme, Steady State Kinetics, and Inhibition by Therapeutic Gold Compounds", The Journal of Biological Chemistry, 1998, pp. 20096-20101, vol. 273, No. 32.

Horinouchi et al., "Photoinduced Nitric Oxide Release from a Nitrobenzene Derivative in Mitochondria", European Journal of Chemistry, 2011, pp. 4809-4813, vol. 17, No. 17.

International Search Report and Written Opinion from related International Application No. PCT/GB2015/051608, dated Oct. 13, 2015, 16 pgs.

Krishna et al., "Oxoammonium cation intermediate in the nitroxide-catalyzed dismutation of superoxide", Proc. Natl. Acad. Sci. USA, 1992, pp. 5537-5541, vol. 89.

Liu et al., "Capture and Visualization of Hydrogen Sulfide via a Fluorescent Probe", Angew Chem Int Ed Engl., 2011, pp. 10327-10329, vol. 50, No. 44.

Luo et al., "Hydrogen sulfide prevents hypoxia-induced apoptosis via inhibition of an H2O2-activated calcium signaling pathway in mouse hippocampal neurons", Biochemical and Biophysical Research Communications, 2012, pp. 473-477, vol. 425.

Monti et al., "Protective Effect of the Nitroxide Tempol Against the Cardiotoxicity of Adriamycin", Free Radical Biology & Medicine, 1996, pp. 463-470, vol. 21, No. 4.

Rapozzi et al., "Nitric oxide-mediated activity in anti-cancer photodynamic therapy", Nitric Oxide, 2013, pp. 26-35, vol. 30.

Tanito et al., "Protective Effect of TEMPOL Derivatives against Light-Induced Retinal Damage in Rats", Investigative Ophthalmology & Visual Science, 2007, pp. 1900-1905, vol. 48, No. 4.

Whiteman et al., "The novel neuromodulator hydrogen sulfide: an endogenous peroxynitrite 'scavenger'?", Journal of Neurochemistry, 2004, pp. 765-768, vol. 90, No. 3.

Whiteman et al., "Hydrogen sulphide: a novel inhibitor of hypochlorous acid-mediated oxidative damage in the brain?", Biochemical and Biophysical Research Communications, 2005, pp. 794-798, vol. 326, No. 4.

Whiteman et al., "Evidence for the formation of a novel nitrosothiol from the gaseous mediators nitric oxide and hydrogen sulphide", Biochemical and Biophysical Research Communications, 2006, pp. 303-310, vol. 343, No. 1.

Berge et al., "Pharmaceutical Salts," Journal of Pharmaceutical Sciences, 1977, pp. 1-19, vol. 66, No. 1.

Bhatia, "Hydrogen Sulfide as a Vasodilator," IUBMB Life, 2005, pp. 603-606, vol. 57, No. 9.

Bhatia et al., "Treatment with H2S-Releasing Diclofenac Protects Mice Against Acute Pancreatitis-Associated Lung Injury," SHOCK, 2008, pp. 84-88, vol. 29, No. 1.

Caliendo et al., "Synthesis and Biological Effects of Hydrogen Sulfide (H2S): Development of H2S-Releasing Drugs as Pharmaceuticals," Journal of Medicinal Chemistry, 2010, pp. 6275-6286, vol. 53, No. 17.

Carballal et al., "Reactivity of hydrogen sulfide with peroxynitrite and other oxidants of biological interest," Free Radical Biology & Medicine, 2011, pp. 196-205, vol. 50.

Chopra et al., "Contrasting Effects of 'Fast' and 'Slow' Releasing H2S Donors on ß Cell Viability in the Diabetic Milieu," Free Radical Biology & Medicine, 2010, p. S43, vol. 49, Suppl. 1.

Eghbal et al., "H2S cytotoxicity mechanism involves reactive oxygen species formation and mitochondrial depolarisation," Toxicology, 2004, pp. 69-76, vol. 203.

EPA, "Toxicological Review of Hydrogen Sulfide," U.S. Environmental Protection Agency, Washington, DC, Jun. 2003, (CAS No. 7783-06-4), 74 pgs.

Fiorucci et al., "Hydrogen Sulfide-Based Therapies: Focus on H2S Releasing NSAIDs," Inflammation & Allergy—Drug Targets, 2011, pp. 133-140, vol. 10, No. 2.

Fox et al., "Inducible hydrogen sulfide synthesis in chondrocytes and mesenchymal progenitor cells: is H2S a novel cytoprotective mediator in the inflamed joint?," Journal of Cellular and Molecular Medicine, 2012, pp. 896-910, vol. 16, No. 4.

Fujita et al., "A Fatal Case of Acute Hydrogen Sulfide Poisoning Caused by Hydrogen Sulfide: Hydroxocobalamin Therapy for Acute Hydrogen Sulfide Poisoning," Journal of Analytical Toxicology, 2011, pp. 119-123, vol. 35.

GB Search Report from related GB Application No. GB1117095.8, dated Jan. 23, 2012; 5 pgs.

Guidotti, "Occupational exposure to hydrogen sulfide in the sour gas industry: some unresolved issues," Int Arch Occup Environ Health, 1994, pp. 153-160, vol. 66.

Horton et al., "Mitochondria-Penetrating Peptides," Chemistry & Biology, 2008, pp. 375-382, vol. 15.

Hoye et al., "Targeting Mitochondria," Accounts of Chemical Research, 2008, pp. 87-97, vol. 41, No. 1.

International Preliminary Report on Patentability from related International Application No. PCT/GB2012/052424, dated Apr. 1, 2014; 7 pgs.

International Search Report and Written Opinion from related International Application No. PCT/GB2012/052424, dated Feb. 8, 2013; 13 pgs.

Kage et al., "Fatal hydrogen sulfide poisoning at a dye works," Legal Medicine, 2004, pp. 182-186, vol. 6.

Kanai et al., "Mitochondrial targeting of radioprotectants using peptidyl conjugates," Org. Biomol. Chem., 2007, pp. 307-309, vol. 5, No. 2.

Kang et al., "Combinatorial drug design targeting multiple cancer signaling networks controlled by mitochondrial Hsp90," The Journal of Clinical Investigation, 2009, pp. 454-464, vol. 119, No. 3.

(56) References Cited

OTHER PUBLICATIONS

Kozlov et al., "Phosphorus-substituted carbothioamides," Russian Chemical Bulletin, International Edition, Apr. 2004, pp. 925-931, vol. 53, No. 4.

Kozlov et al., "Factors Determining the Stereochemical Structure of 2-(Phosphorus Substituted) Methylidene-thiazolidine-4-ones in Solid State and in Solution," Phorphorus, Sulfur, and Silicon, 2009, pp. 830-845, vol. 184, No. 4.

Lee et al., "Effects of Hydrogen Sulfide-releasing L-DOPA Derivatives on Glial Activation," The Journal of Biological Chemistry, 2010, pp. 17318-17328, vol. 285, No. 23.

Lee et al., "The Slow-Releasing Hydrogen Sulfide Donor, GYY4137, Exhibits Novel Anti-Cancer Effects In Vitro and In Vivo," PLoS ONE, 2011, e21077, pp. 1-7, vol. 6, No. 6.

Li et al,, "Characterization of a Novel, Water-Soluble Hydrogen Sulfide-Releasing Molecule (GYY4137): New Insights Into the Biology of Hydrogen Sulfide," Circulation, 2008, pp. 2351-2360, vol. 117, No. 18.

Li et al. "GYY4137, a novel hydrogen sulfide-releasing molecule, protects against endotoxic shock in the rat," Free Radical Biology & Medicine, 2009, pp. 103-113, vol. 47, No. 1.

Lisjak et al., "A novel hydrogen sulfide donor causes stomatal opening and reduces nitric oxide accumulation," Plant Physiology and Biochemistry, 2010, pp. 931-935, vol. 48, No. 12.

Maebashi et al., "Toxicological analysis of 17 autopsy cases of hydrogen sulfide poisoning resulting from the Inhalation of intentionally generated hydrogen sulfide gas," Forensic Science International, 2011, pp. 91-95, vol. 207.

Maiti et al., "Guanidine-Containing Molecular Transporters: Sorbitol-Based Transporters Show High Intracellular Selectivity toward Mitochondria," Angew. Chem. Int. Ed., 2007, pp. 5880-5884, vol. 46.

Malekova et al., "H2S and HS—donor NaHS inhibits intracellular chloride channels," General Physiology and Biophysics, 2009, pp. 190-194, vol. 28.

Martell et al., "Physiopathology of splanchnic vasodilation in portal hypertension," World Journal of Hepatology, 2010, pp. 208-220, vol. 2, No. 6.

Milby et al., "Hydrogen Sulfide Poisoning: Clarification of Some Controversial Issues," American Journal of Industrial Medicine, 1999, pp. 192-195, vol. 35.

Modica-Napolitano et al., "Selective Damage to Carcinoma Mitochondria by the Rhodacyanine MKT-077," Cancer Research, 1996, pp. 544-550, vol. 56.

Murphy et al., "Targeting Antioxidants to Mitochondria by Conjugation to Lipophilic Cations," Annual Review of Pharmacology and Toxicology, 2007, pp. 629-656, vol. 47.

Olson, "The therapeutic potential of hydrogen sulfide: separating hype from hope," American Journal of Physiology—Regulatory Integrative and Comparative Physiology, 2011, pp. R297-R312, vol. 301, No. 2.

OSHA Fact Sheet, "Hydrogen Sulfide (H2S)," U.S. Department of Labor, Oct. 2005, 2 pgs.

Predmore et al., "Hydrogen sulfide-mediated myocardial pre- and post-conditioning," Expert Review of Clinical Pharmacology, 2011, pp. 83-96, vol. 4, No. 1.

Querellou et al., "Intoxication accidentelle mortelle par hydrogene sulfure Fatal outcome of an hydrogen sulfide poisoning," Annales Francaises d' Anesthesie et de Reanimation, 2005, pp. 1302-1304, vol. 24.

Quintanilla et al., "Caspase-cleaved Tau Expression Induces Mitochondrial Dysfunction in Immortalized Cortical Neurons," The Journal of Biological Chemistry, 2009, pp. 18754-18766, vol. 284, No. 28.

Rafalowska et al., "Metabolic Changes in Rat Brain Synaptosomes After Exposure to Sulfide in Vivo," Toxicology Letters, 1986, pp. 193-200, vol. 34.

Nicholson et al., "Inhibition of Respiratory and Bioenergetic Mechanisms by Hydrogen Sulfide in Mammalian Brain," Journal of Toxicology and Environmental Health, Part A: Current Issues, 1998, pp. 491-507, vol. 54.

Senkal et al., "Potent Antitumor Activity of a Novel Cationic Pyridinium-Ceramide Alone or in Combination with Gemcitabine against Human Head and Neck Squamous Cell Carcinomas in Vitro and in Vivo," The Journal of Pharmacology and Experimental Therapeutics, 2006, pp. 1188-1199, vol. 317, No. 3.

D'Souza et al., "DQAsome-mediated delivery of plasmid DNA toward mitochondria in living cells," Journal of Controlled Release, 2003, pp. 189-197, vol. 92.

D'Souza et al., "Mitochondrial leader sequence-plasmid DNA conjugates delivered into mammalian cells by DQAsomes co-localize with mitochondria," Mitochondrion, 2005, pp. 352-358, vol. 5.

Tazzari et al., "New aryldithiolethione derivatives as potent histone deacetylase inhibitors," Bioorganic & Medicinal Chemistry, 2010, pp. 4187-4194, vol. 18.

Truong et al., "Molecular Mechanisms of Hydrogen Sulfide Toxicity," Drug Metabolism Reviews, 2006, pp. 733-744, vol. 38.

Vacek et al., "Hydrogen sulfide protects against vascular remodeling from endothelial damage," Amino Acids, 2010, pp. 1161-1169, vol. 39.

Vauzour et al., "Champagne Wine Polyphenols Protect Primary Cortical Neurons against Peroxynitrite-Induced Injury," Journal of Agricultural and Food Chemistry, 2007, pp. 2854-2860, vol. 55, No. 8.

Virieux et al., "A review of methods to prepare alkylphosphonium salts," Science of Synthesis, 2009, vol. 42; English Abstract Only.

Wagner, "Hydrogen sulfide: a new gaseous signal molecule and blood pressure regulator," Journal of Nephrology, 2009, pp. 173-176, vol. 22.

Wallace et al., "Gastrointestinal Safety and Anti-Inflammatory Effects of a Hydrogen Sulfide-Releasing Diclofenac Derivative in the Rat," Gastroenterology, 2007, pp. 261-271, vol. 132.

Wang et al., "Generation of a Stable Antioxidant Response Element-Driven Reporter Gene Cell Line and Its Use to Show Redox-Dependent Activation of Nrf2 by Cancer Chemotherapeutic Agents," Cancer Research, 2006, pp. 10983-10994, vol. 66, No. 22.

Wang et al., "Cu-Labeled Triphenylphosphonium and Triphenylarsonium Cations as Highly Tumor-Selective Imaging Agents," Journal of Medicinal Chemistry, 2007, pp. 5057-5069, vol. 50, No. 21.

Warenycia et al., "Monoamine oxidase inhibition as a sequel of hydrogen sulfide intoxication: increases in brain catecholamine and 5-hydroxytryptamine levels," Archives of Toxicology, 1989, pp. 131-136, vol. 63.

Warenycia et al., "Acute Hydrogen Sulfide Poisoning: Demonstration of Selective Uptake of Sulfide by the Brainstem by Measurement of Brain Sulfide Levels," Biochemical Pharmacology, 1989, pp. 973-981, vol. 38, No. 6.

Weiss et al., "Dequalinium, a topical antimicrobial agent, displays anticarcinoma activity based on selective mitochondrial accumulation," PNAS, 1987, pp. 5444-5448, vol. 84.

Whiteman et al., "Peroxynitrite mediates calcium-dependent mitochondrial dysfunction and cell death via activation of calpains," The FASEB Journal, 2004, 35 pgs., vol. 18.

Whiteman et al., "Detection and Measurement of Reactive Oxygen Intermediates in Mitochondria and Cells," Methods in Molecular Biology, 2008, pp. 29-50, vol. 476.

Whiteman et al., "Hydrogen sulfide and the vasculature: a novel vasculoprotective entity and regulator of nitric oxide bioavailability?," J. Cell. Mol. Med., 2009, pp. 488-507, vol. 13, No. 3.

Whiteman et al., "Hydrogen sulfide and inflammation: the good, the bad, the ugly and the promising," Expert Reviews in Clinical Pharmacology, 2011, pp. 13-32, vol. 4, No. 1.

Yoshida et al., "α-Thiocarbonyl-stabilized Triphenylphosphonium Ylides: Preparation, Structure, and Alkylation Reactions," Bulletin of the Chemical Society of Japan, 1975, pp. 2907-2910, vol. 48, No. 10.

Zabbarova et al., "Targeted Delivery of Radioprotective Agents to Mitochondria," Mol. Interv., 2008, pp. 294-302, vol. 8, No. 6.

(56) References Cited

OTHER PUBLICATIONS

Zhang et al., "Role of Hydrogen Sulfide in Severe Burn Injury—Induced Inflammation in Mice," Mol. Med., 2010, pp. 417-424, vol. 16.

Zimmer et al., "Effect of the triaminopyridine flupirtine on calcium uptake, membrane potential and ATP synthesis in rat heart mitochondria," British Journal of Pharmacology, 1998, pp. 1154-1158, vol. 123, No. 6.

\* cited by examiner

Protective effect of GYY4137 against SIN-1 after 24hrs

Effect of H2S donors on ROS production in presence of 4-HNE

Pre-treatment of THP-1 cells with H$_2$S donors followed by 1min treatment with H$_2$O$_2$ 25μM Prx 3

*p= 0.0320
** p< 0.005
*** p= 0.0007
**** p< 0.0001
n=3, unpaired t-test

HYDROGEN SULFIDE RELEASING COMPOUNDS AND THEIR USE

FIELD OF THE INVENTION

The invention relates to a compound comprising a mitochondrial targeting group linked to a group capable of releasing hydrogen sulfide for use in the treatment of the human or animal body by surgery or therapy, to the use of this compound in the treatment of a plant, and to novel compounds.

BACKGROUND TO THE INVENTION

It is well established that $H_2S$ is a physiological gaseous mediator in humans and animals. More recently, it has also been found that $H_2S$ is a gaseous mediator in plants (M. Lisjak et al, Plant Physiol. Biochem., 2010, 48(12), 931-5).

In humans and animals, $H_2S$ is synthesised primarily from L-cysteine and homocysteine from the pyridoxal phosphate-dependent enzymes cystathionine-β-synthase (CBS) and cystathionine-γ-lyase (CSE). At present, it is thought that CBS is found primarily in nervous tissue, whereas CSE is expressed in vascular and inflammatory cells (M. Whiteman et al, J. Cell Mol. Med., 2009; 13:488-507; and M. Whiteman et al, Expert Reviews in Clinical Pharmacology, 2011, 4, 13-32). The generation of $H_2S$ in human and other mammalian tissues is likely to occur at a slow and constant rate, and it appears to be involved in several processes, such as hypertension, inflammation, edema and hemorrhagic shock (G. Caliendo et al, J. Med. Chem., 2010, 53(17), 6275-6286). Compounds that are able to slowly release $H_2S$ in vivo are therefore likely to have therapeutic applications in the treatment of diseases or disorders involving such processes.

It has also been found that compounds that are able to slowly release hydrogen sulfide in vivo are able to prevent stomatal closure in plants (M. Lisjak et al, Plant Physiol. Biochem., 2010, 48(12), 931-5). Compounds that slowly release $H_2S$ in vivo in plants may promote plant growth or can be used as a herbicidal treatment.

SUMMARY OF THE INVENTION

Hydrogen sulfide is rapidly oxidized, mainly in the mitochondria of cells, initially to thiosulfate and then to sulfite and sulfate. Mitochondria are key intracellular organelles that are involved in cell death (survival, apoptosis or necrotic cell death) and are key regulators of cell and tissue function in health and disease.

The invention relates to uses of a compound comprising a mitochondrial targeting group linked to a group capable of releasing hydrogen sulfide, or a pharmaceutically acceptable salt thereof. These compounds can be used to selectively and slowly release $H_2S$ in vivo directly to, or in the vicinity of, the mitochondria in cells. The compounds can be used to provide excellent bioavailability of hydrogen sulfide in cells.

In an aspect of the invention, the compound comprising a mitochondrial targeting group linked to a group capable of releasing hydrogen sulfide, or a pharmaceutically acceptable salt thereof, is for use in the treatment of the human or animal body by surgery or therapy.

In an embodiment, the compound is for use in the treatment or prevention of a disease or disorder susceptible to amelioration by in vivo release of hydrogen sulfide.

According to a further aspect of the invention, there is provided the use of the compound comprising a mitochondrial targeting group linked to a group capable of releasing hydrogen sulfide in the manufacture of a medicament for use in the treatment of a disease or disorder susceptible to amelioration by in vivo release of hydrogen sulfide.

According to a further aspect of the invention, there is provided a method of treating a patient suffering from or susceptible to a disease or disorder susceptible to amelioration by in vivo release of hydrogen sulfide, which method comprises administering to said patient a compound comprising a mitochondrial targeting group linked to a group capable of releasing hydrogen sulfide, or a pharmaceutically acceptable salt thereof.

According to a further aspect of the invention, there is provided a pharmaceutical composition comprising the compound which comprises a mitochondrial targeting group linked to a group capable of releasing hydrogen sulfide, or a pharmaceutically acceptable salt thereof, and a pharmaceutically acceptable excipient, diluent or carrier.

According to a further aspect of the invention, there is provided a combination comprising (i) the compound comprising a mitochondrial targeting group linked to a group capable of releasing hydrogen sulfide, or a pharmaceutically acceptable salt thereof, and (ii) an active agent suitable for use in the treatment of the human or animal body by surgery or therapy.

According to a further aspect of the invention, there is provided the use of a compound comprising a mitochondrial targeting group linked to a group capable of releasing hydrogen sulfide, or a pharmaceutically acceptable salt thereof, in a treatment of a plant to promote plant growth.

According to a further aspect of the invention, there is provided the use of a compound comprising a mitochondrial targeting group linked to a group capable of releasing hydrogen sulfide, or a pharmaceutically acceptable salt thereof, in a herbicidal treatment of a plant.

According to a further aspect of the invention, there is provided the use of a compound comprising a mitochondrial targeting group linked to a group capable of releasing hydrogen sulfide to prevent or reduce stomatal closure or to cause stomatal opening in a plant.

The uses of the invention that relate to the treatment of plants, such as by preventing or reducing stomatal closure or by causing stomatal opening in a plant, also relate to a method that comprises the step of treating a plant with the compound as defined below. The method may be for treating a plant to promote plant growth; for herbicidally treating a plant; or for preventing or reducing stomatal closure or for causing stomatal opening in a plant.

According to a further aspect of the invention, there is provided a compound of the formula:

MTG-L-S wherein:

S is a group capable of releasing hydrogen sulfide selected from:

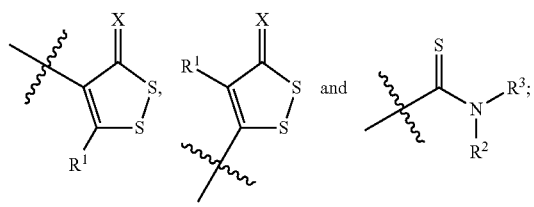

X represents S, O or N—OH;

$R^1$, $R^2$ and $R^3$ each independently represent hydrogen, $C_{1-12}$ alkyl, $C_{1-12}$ alkoxy or $C_{6-10}$ aryl, wherein each $C_{1-12}$ alkyl, $C_{1-12}$ alkoxy or $C_{6-10}$ aryl group is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and halo-$C_{1-12}$-alkoxy substituents;

L is a linker represented by formula:

–L'–Y–Z– wherein:

L' is a straight chain alkylene group having the formula

–(CH$_2$)$_n$– wherein n is an integer from 2 to 19;
Y represents a direct bond, –OC(O)– or –C(O)O–;
Z represents a direct bond or a phenylene group, which is unsubstituted or substituted by one, two, three or four substituents selected from a halogen atom, hydroxy, $C_{1-12}$ alkyl and a $C_{1-12}$ alkoxy group;
and MTG represents a mitochondrial targeting group;
or a pharmaceutically acceptable salt thereof.

DETAILED DESCRIPTION OF THE INVENTION

Figure 1:
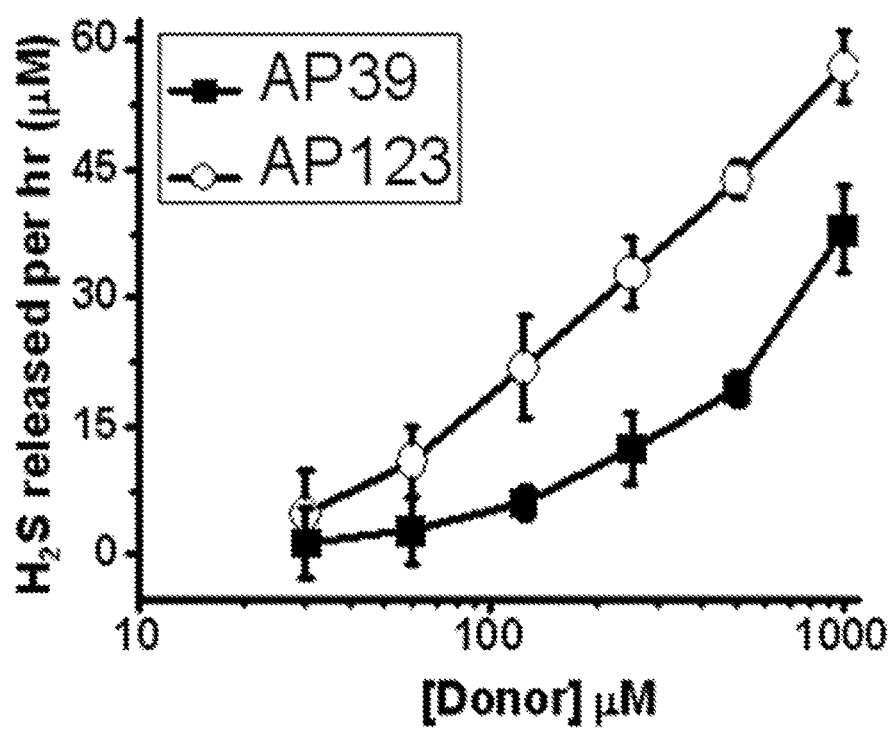
FIG. 1 is a graph showing the rate of $H_2S$ release for the compounds AP39 (see Example 1) and AP123 (see Example 8) as measured by zinc trap spectrophotometry.

The invention is concerned with compounds which comprise a group that is capable of releasing hydrogen sulfide. Typically, the group is capable of releasing hydrogen sulfide in vivo. In general, the group undergoes a reaction in vivo to generate $H_2S$ or $HS^-$.

Generally, the group is a moiety capable of releasing hydrogen sulfide that is linked, either directly or via a linker (L), to a mitochondrial targeting group. The mitochondrial targeting group can be attached at any convenient position on the compound that is capable of releasing hydrogen sulfide.

Compounds capable of releasing hydrogen sulfide are well known in the art, see for example G. Caliendo et al (J. Med. Chem., 2010, 53(17), 6275-6286). Examples of compounds capable of releasing hydrogen sulfide include N-acetyl-penicillamine, S-allyl-cysteine, bucillamine, carbocysteine, cysteamine, cystathionine, homocysteine, mecysteine, methionine, pantetheine, penicillamine, penicillamine disulfide, thioacetic acid, thiodiglycolic acid, thioglycolic acid, thiolactic acid, 2-thiolhistidine, thiomalic acid, thiosalicylic acid, tiopronin, 5-(p-hydroxyphenyl)-3H-1,2-dithiol-3-thione, 1,3-dithiol-2-thione-5-carboxylic acid, 3-thioxo-3H-1,2-dithiole-5-carboxylic acid and 3-thioxo-3H-1,2-dithiole-4-carboxylic acid.

The group capable of releasing hydrogen sulfide can, for example, comprise a sulfide, a disulfide or a polysulfide moiety.

In an embodiment, the group capable of releasing hydrogen sulfide comprises a thiocarbamoyl group, a 5-thioxo-5H-1,2-dithiol-3-yl group, a 5-thioxo-5H-1,2-dithiol-4-yl group, a 5-oxo-5H-1,2-dithiol-3-yl group, a 5-oxo-5H-1,2-dithiol-4-yl group, a 5-hydroxyimino-5H-1,2-dithiol-3-yl group, a 5-hydroxyimino-5H-1,2-dithiol-4-yl group, a phosphinodithioate group or a phosphinodithioic acid group. In an embodiment, the group capable of releasing hydrogen sulfide is a thiobenzamide group (thiobenzamidyl) or a 5-thioxo-5H-1,2-dithiol-3-yl group.

In an embodiment, the group capable of releasing hydrogen sulfide (S) is selected from:

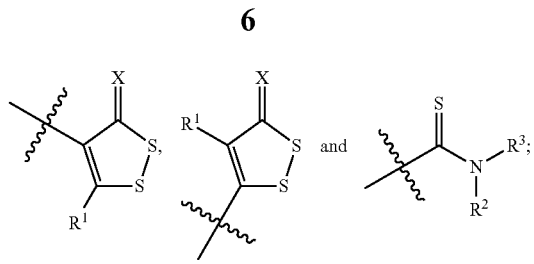

wherein:
X represents S, O or N—OH;
$R^1$, $R^2$ and $R^3$ each independently represent hydrogen, $C_{1-12}$ alkyl, $C_{1-12}$ alkoxy or $C_{6-10}$ aryl, wherein each $C_{1-12}$ alkyl, $C_{1-12}$ alkoxy or $C_{6-10}$ aryl group is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and halo-$C_{1-12}$-alkoxy substituents.

In an embodiment, X is S or O. In an embodiment, X is S.

In an embodiment, $R^1$, $R^2$ and $R^3$ each independently represent hydrogen, $C_{1-12}$ alkyl, or $C_{1-12}$ alkoxy. In an embodiment, $R^1$, $R^2$ and $R^3$ each independently represent hydrogen, or $C_{1-12}$ alkyl. In an embodiment, $R^1$, $R^2$ and $R^3$ each independently represent hydrogen.

In an embodiment, the group capable of releasing hydrogen sulfide (S) is selected from:

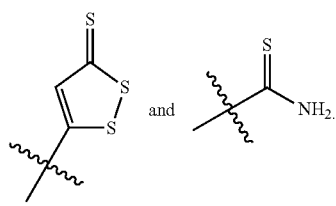

A mitochondrial targeting group is a group which is capable of concentrating the compound in the mitochondria of a cell. For example, following incubation of a cell with a compound comprising a mitochondrial targeting group, the concentration of the compound in the mitochondria will be higher than the concentration of conjugate in the cytosol. Mitochondrial targeting groups are well known and examples of appropriate mitochondrial targeting groups are discussed in Souza et al (Mitochondrion 5 (2005) 352-358), Kang et al (The Journal of Clinical Investigation, 119, 3, 454-464), Horton et al (Chemistry and Biology 15, 375-382), Wang et al (J. Med. Chem., 2007, 50 (21), 5057-5069), Souza et al (Journal of Controlled Release 92 (2003) 189-197), Maiti et al (Angew. Chem. Int. Ed., 2007, 46, 5880-5884), Kanai et al (Org. Biomol. Chem., 2007, 5, 307-309), Senkal et al (J Pharmacol Exp Ther., 317(3), 1188-1199), Weiss et al (Proc Natl Acad Sci USA, 84, 5444-5488), Zimmer et al (Br J Pharmacol., 1998, 123(6), 1154-8), Modica-Napolitano et al (Cancer Res., 1996, 56, 544-550), Murphy et al (Ann Rev. Pharm Toxicol., (2007), 47, 629-656), and Hoye et al (Accounts of Chemical Research, 41, 1, 87-97).

All of the above documents are incorporated by reference. For the avoidance of doubt, all of the mitochondrial targeting groups disclosed in these articles can be used in the compounds comprising a mitochondrial targeting group linked to a group capable of releasing hydrogen sulfide.

In an embodiment, the mitochondrial targeting group is a group which is capable of concentrating the compound specifically in the mitochondrial matrix of a cell.

In an embodiment, the mitochondrial targeting group (MTG) is a lipophilic cation or a mitochondrial targeting peptide. In an embodiment, the lipophilic cation is a phosphonium cation, an arsonium cation, an ammonium cation, flupritine, MKT-077, a pyridinium ceramide, a quinolium, a liposomal cation, a sorbitol guanidine, a cyclic guanidine or a rhodamine.

Flupritine and MKT-077 are described in Zimmer et al. (Br J Pharmacol., 1998, 123(6), 1154-8) and Modica-Napolitano et al (Cancer Res., 1996, 56, 544-550). Mitochondrial targeting peptides are described in Horton et al (Chemistry and Biology 15, 375-382) and Hoye et al (Accounts of Chemical Research, 41, 1, 87-97).

In an embodiment, the mitochondrial targeting group (MTG) is a phosphonium cation. In an embodiment, the phosphonium cation has the formula:

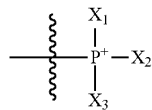

wherein $X_1$, $X_2$ and $X_3$ each independently represent $C_{1-12}$ alkyl, $C_{6-10}$ aryl, or $C_{1-12}$alkylene-$C_{6-10}$-aryl, wherein the alkyl and alkylene groups and moieties are unsubstituted or substituted by one or more, for example 1, 2 or 3, halogen atoms, hydroxyl, $C_{1-12}$ alkoxy or halo-$C_{1-12}$-alkoxy groups, and each aryl group or moiety is unsubstituted or substituted by one, two or three halogen atoms, hydroxyl, $C_{1-12}$ alkoxy or halo-$C_{1-12}$-alkoxy groups.

In an embodiment, each alkyl or alkylene group or moiety is unsubstituted or substituted by one or more, such as 1 or 2, halogen atoms. In an embodiment, the alkyl and/or alkylene group or moiety is unsubstituted.

In an embodiment, $X_1$, $X_2$ and $X_3$ are each a $C_{6-10}$ aryl group, for example a phenyl group. In an embodiment, $X_1$, $X_2$ and $X_3$ are the same.

In an embodiment, the mitochondrial targeting group is a triphenylphosphonium cation of the formula:

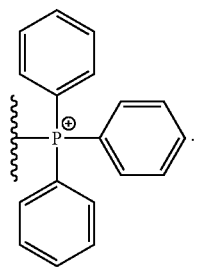 [SMILES: *[P+](c1ccccc1)(c1ccccc1)c1ccccc1]

The group capable of releasing hydrogen sulfide may be linked to one, two, three or more mitochondrial targeting groups. When the group capable of releasing hydrogen sulfide is linked to more than one mitochondrial targeting group, each mitochondrial targeting group can be the same or different. In an embodiment, the group capable of releasing hydrogen sulfide is linked to one mitochondrial targeting group.

In an embodiment, the mitochondrial targeting group is covalently linked to the group capable of releasing hydrogen sulfide.

The or each mitochondrial targeting group can be linked to the group capable of releasing hydrogen sulfide directly or via a linker (L). Where there is more than one mitochondrial targeting group, all of the mitochondrial targeting groups can be covalently linked directly to the group capable of releasing hydrogen sulfide or all of the mitochondrial targeting groups can be linked via a linker to the group capable of releasing hydrogen sulfide.

In an embodiment, there is one mitochondrial targeting group that is linked via a linker to the group capable of releasing hydrogen sulfide.

The linker (L) can be any moiety capable of linking a mitochondrial targeting group to the group capable of releasing hydrogen sulfide.

The linker (L) may have a molecular weight of 14 to 1000, such as 28 to 500, for example 44 to 300.

In an embodiment, the linker (L) is a direct bond or is a $C_{1-20}$ alkylene which is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and a halo-$C_{1-12}$-alkoxy group, wherein zero or one to ten carbon atoms in the alkylene chain are replaced by spacer moieties selected from $C_{6-10}$ arylene, —O—, —S—, —NR$^4$—, —C(O)NR$^4$—, —NR$^4$C(O)—, —C(O)—, —OC(O)—, —C(O)O— moieties, wherein $R^4$ is hydrogen or $C_{1-12}$ alkyl and the $C_{6-10}$ arylene moiety is unsubstituted or substituted by one, two, three or four substituents selected from a halogen atom, hydroxy, $C_{1-12}$ alkyl and a $C_{1-12}$ alkoxy group.

In an embodiment, the spacer moieties are selected from $C_{6-10}$ arylene, —O—, —S—, —NR$^4$—, —C(O)NR$^4$—, —NR$^4$C(O)—, —C(O)—, —OC(O)—, —C(O)O— moieties. In an embodiment, the alkylene group consists of 1, 2, 3, 4 or 5 spacer moieties. In an embodiment, the alkylene group consists of 1 to 3 spacer moieties. In an embodiment, the alkylene group consists of 1 or 2 spacer moieties.

In an embodiment, the spacer moieties comprise 0 to 2 $C_{6-10}$ arylene, 0 to 2 —S—, 0 to 2 —O—, 0 to 2 —NR$^4$—, 0 to 2 —C(O)NR$^4$—, 0 to 2 —NR$^4$C(O)—, 0 to 2 —C(O)—, 0 to 2 —OC(O)—, and 0 to 2 —C(O)O— moieties. In an embodiment, the linker comprises at least one $C_{6-10}$ arylene and at least one of the —OC(O)— or —C(O)O— spacer moieties.

In an embodiment, the alkylene group is a $C_{1-20}$ alkylene. In an embodiment, the alkylene group is a $C_{2-18}$ alkylene, such as a $C_{3-16}$ alkylene.

In an embodiment, the alkylene is a straight chain alkylene.

In an embodiment, the alkylene is unsubstituted or substituted by one or more, such as 1 or 2, halogen atoms. In an embodiment, said alkylene group is unsubstituted.

In an embodiment, the arylene spacer moiety is unsubstituted or substituted with one, two or three halogen atoms, hydroxy groups or $C_{1-12}$ alkyl groups. When the arylene spacer moiety carries 2 or more substituents, the substituents may be the same or different. In an embodiment, the arylene spacer moiety is unsubstituted.

In an embodiment, the linker (L) is represented by the formula:

-L'-Y—Z— wherein:

L' represents a direct bond or a straight chain $C_{1-20}$ alkylene group, such as a straight chain $C_{2-18}$ alkylene group, which is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and a halo-$C_{1-12}$-alkoxy group;

Y represents a direct bond, —OC(O)— or —C(O)O—;

Z represents a direct bond or a phenylene group, which is unsubstituted or substituted by one, two, three or four substituents selected from a halogen atom, hydroxy, $C_{1-12}$ alkyl and a $C_{1-12}$ alkoxy group.

In an embodiment, the alkylene group is unsubstituted or is substituted with one, two or three substituents selected from a halogen atom, hydroxy, $C_{1-12}$ alkoxy, $C_{1-12}$ alkyl. In an embodiment, the alkylene group is unsubstituted.

In an embodiment, L' is a straight chain alkylene group having the formula:

where n is an integer from 1 to 19.

In an embodiment, n is an integer from 2 to 19. In an embodiment, n is an integer from 2 to 18, from 2 to 17, from 2 to 16, from 2 to 15, from 3 to 19, from 3 to 18, from 3 to 17, from 3 to 16, from 3 to 15, from 4 to 19, from 4 to 18, from 4 to 17, from 4 to 16, or from 4 to 15. In an embodiment, n is either 2, 4, 5, 7, 9, 11 or 15.

In an embodiment, Y is a —C(O)O— group.

In an embodiment, Z is a para-phenylene group.

In an embodiment, the moiety —Y—Z— has the formula:

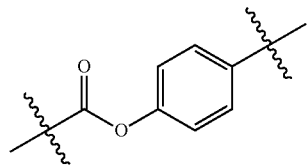

In an embodiment, a compound comprising a mitochondrial targeting group linked to a group capable of releasing hydrogen sulfide is represented by the formula:

MTG-L-S wherein:

S is a group capable of releasing hydrogen sulfide selected from:

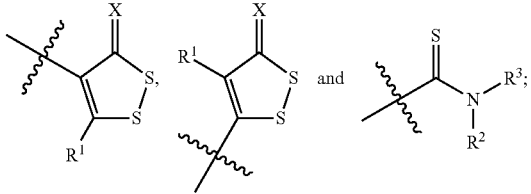

X represents S, O or N—OH;

$R^1$, $R^2$ and $R^3$ each independently represent hydrogen, $C_{1-12}$ alkyl, $C_{1-12}$ alkoxy or $C_{6-10}$ aryl, wherein each $C_{1-12}$ alkyl, $C_{1-12}$ alkoxy or $C_{6-10}$ aryl group is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and halo-$C_{1-12}$-alkoxy substituents;

L represents a direct bond or a linker, wherein the linker is a $C_{1-20}$ alkylene which is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and a halo-$C_{1-12}$-alkoxy group, wherein zero or one to ten carbon atoms in the alkylene chain are replaced by spacer moieties selected from $C_{6-10}$ arylene, —O—, —S—, —$NR^4$—, —C(O)$NR^4$—, —$NR^4$C(O)—, —C(O)—, —OC(O)—, —C(O)O— moieties, wherein $R^4$ is hydrogen or $C_{1-12}$ alkyl and the $C_{6-10}$ arylene moiety is unsubstituted or substituted by one, two, three or four substituents selected from a halogen atom, hydroxy, $C_{1-12}$ alkyl and a $C_{1-12}$ alkoxy group; and MTG represent a mitochondrial targeting group, such as, for example, a phosphonium cation;

or a pharmaceutically acceptable salt thereof.

In the compounds that have the formula MTG-L-S, the mitochondrial targeting group (MTG), the linker (L) and the group capable of releasing hydrogen sulfide (S) can be as defined above.

In an embodiment, the compound comprises a cation selected from:

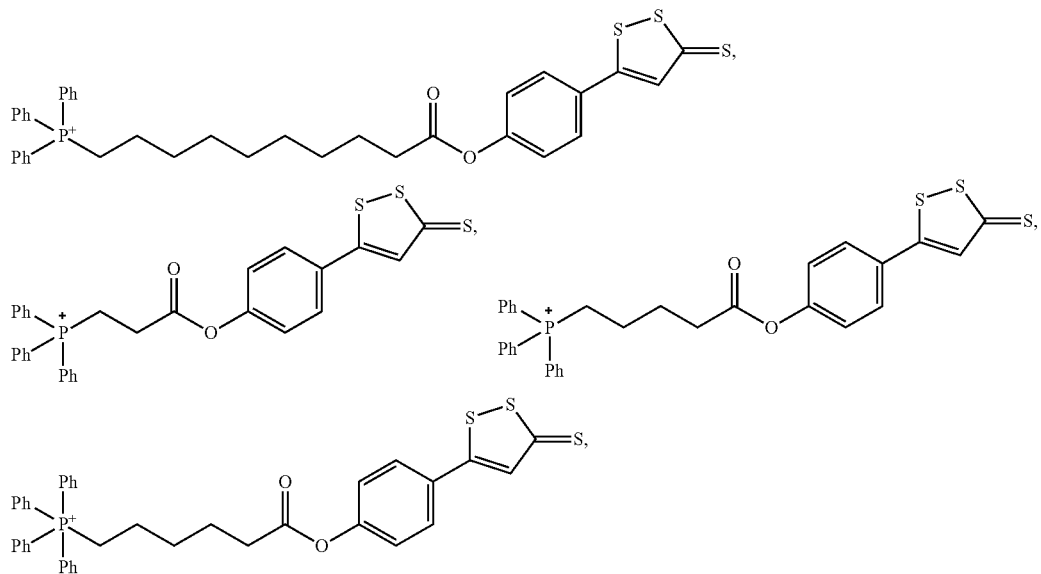

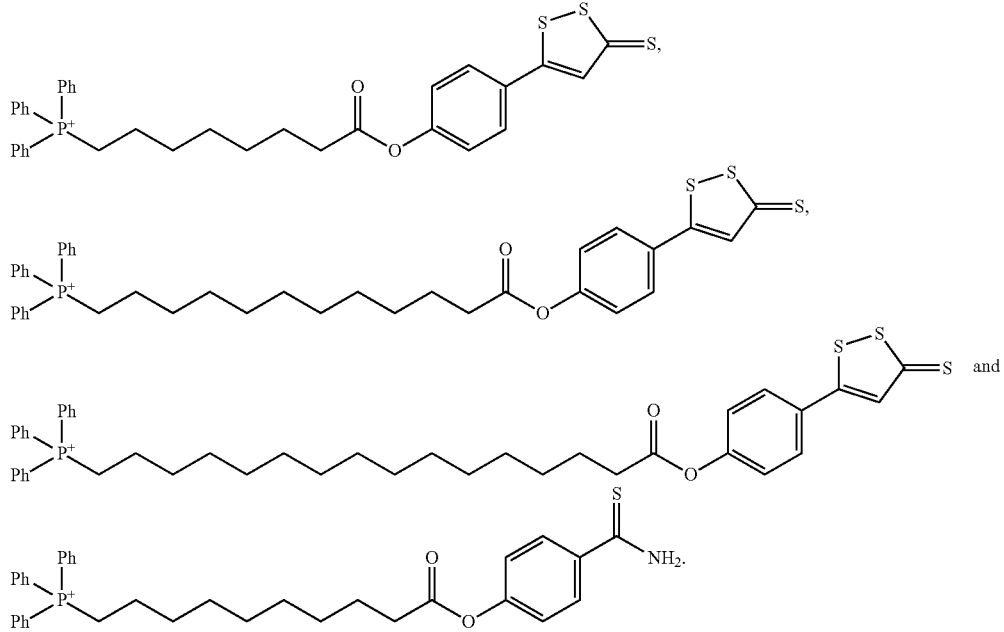

In an embodiment, the compound comprising a mitochondrial targeting group linked to a group capable of releasing hydrogen sulfide comprises a cation having a structure as set out above and an anion that is a halogen (i.e. $F^-$, $Cl^-$ or $Br^-$). In an embodiment, the anion is a bromide anion.

The compounds comprising a mitochondrial targeting group linked to a group capable of releasing hydrogen sulfide can be prepared using the methods described herein or by routine modifications thereof, or by using conventional methods known in the art.

Treatment of Humans or Animals

The compound comprising a mitochondrial targeting group linked to a group capable of releasing hydrogen sulfide may be used in the treatment of the human or animal body by surgery or therapy. In an embodiment, the animal is a mammal.

A compound comprising a mitochondrial targeting group linked to a group capable of releasing hydrogen sulfide can be used in the treatment or prevention of a disease or disorder susceptible to amelioration by in vivo release of hydrogen sulfide.

The invention also relates to the use of the compound in the manufacture of a medicament for use in the treatment of a disease or disorder susceptible to amelioration by in vivo release of hydrogen sulfide.

The invention also provides a method of treating a patient suffering from or susceptible to a disease or disorder susceptible to amelioration by in vivo release of hydrogen sulfide, which method comprises administering to said patient a compound comprising a mitochondrial targeting group linked to a group capable of releasing hydrogen sulfide.

Surprisingly, the compounds comprising a mitochondrial targeting group linked to a group capable of releasing hydrogen sulfide enhance the bioavailability of hydrogen sulfide in cells, particularly in comparison to other compounds that are capable of releasing hydrogen sulfide which do not have a mitochondrial targeting group.

In an embodiment, the disease or disorder susceptible to amelioration by in vivo release of hydrogen sulfide is a chronic inflammatory disease or disorder, an acute inflammatory disease or disorder, a disease or disorder associated with mitochondrial dysfunction, a disease or disorder associated with micro- or macro-angiopathy, a neurodegenerative disease, a disease or disorder associated with ageing, a disease or disorder associated with organ failure, a disease or disorder associated with acute and/or chronic renal insults, or a disease or disorder associated with the abnormal proliferation of cells.

Examples of a chronic inflammatory disease or disorder include an inflammatory joint disease (e.g. rheumatoid arthritis), asthma, chronic obstructive pulmonary disease, ulcerative colitis, inflammatory bowel disease, hepatitis or atherosclerosis.

Examples of an acute inflammatory disease or disorder include endotoxic shock (e.g. sepsis) or hemorrhagic shock.

Examples of a disease or disorder associated with mitochondrial dysfunction include osteoarthritis, osteoporosis or diabetes (type I and type II, e.g. type II diabetes).

Examples of a disease or disorder associated with micro- or macro-angiopathy include vascular complications of obesity, diabetes, metabolic syndrome, natural ageing, hypertension, myocardial infarction, ischaemia, ischaemic heart disease, reperfusion injury, hypoxia, ischaemia-reperfusion injury, hypoxia-reperfusion injury, retinopathy or neuropathy. The hypoxia may occur in one or more tissues, such as lung, liver or kidney.

Examples of a neurodegenerative disease include Alzheimer's disease, amyotrophic lateral sclerosis (e.g. motor neuron disease), Parkinson's disease, Huntingdon's disease, a tauopathy, an extrapyramidal and movement disorder, or a neurological disease where the death of neurons, astrocytes or glia are prominent (e.g. ataxia telangiectasia, corticobasal degeneration or progressive supranuclear palsy).

Examples of a disease or disorder associated with ageing include micro-angiopathy, macro-angiopathy or vascular dementia.

A disease or disorder associated with organ failure can relate to organ failure of the lung, kidney or liver.

Examples of a disease or disorder associated with acute and/or chronic renal insults include ischaemia-reperfusion injury, hyperhomocysteinemia and hyperglycemia.

An example of a disease or disorder associated with the abnormal proliferation of cells is cancer.

The production of $H_2S$ has been linked to anti-cancer activity. Specifically, non-targeted $H_2S$ donor compound GYY4137 (morpholin-4-ium 4-methoxyphenyl(morpholino) phosphinodithioate) has been shown to exhibit anti-cancer effects in vitro and in vivo (Lee Z. W. et al., PLoS ONE, 2011, 6(6): e21077).

Generally, any activity shown by non-targeted $H_2S$ donor GYY4137 would also be expected to be shown by mitochondria-targeted $H_2S$ donor AP39, and AP39 would usually be expected to be found to mediate the relevant effect at a significantly lower concentration than GYY4137 (see, for example, the data in FIGS. 4, 14, 15 and 16, together with their discussion).

It has been shown that blood plasma levels of $H_2S$ decrease with age and that low plasma $H_2S$ levels are strongly correlated with higher systemic blood pressure and impaired microvascular function. It is believed that $H_2S$ is vasculoprotective in that it dilates blood vessels and inhibits endothelial dysfunction. It has been shown that endogenous and exogenous $H_2S$ is a vasodilator (Li et al, Circulation, 2008, 117, 2351-60).

There is evidence to suggest that $H_2S$ can act as an antioxidant in vivo. In cell culture experiments, $H_2S$ or $HS^-$ generated from NaSH has been shown to "scavenge" detrimental pro-inflammatory oxidants, such as hydrogen peroxide ($H_2O_2$), superoxide ($O_2.^-$) and nitric oxide (.NO). Compounds that are able to release hydrogen sulfide in vivo may therefore have therapeutic application in the treatment of inflammatory diseases or diseases caused by hyperactive apoptosis (i.e. loss of control of cell death). It has also been shown the compounds that release $H_2S$ slowly have an anti-inflammatory effect in endotoxic shock (Li et al, Free Radical Biology & Medicine, 2009, 47, 103-113).

Blood plasma levels of $H_2S$ decrease with age. It has also been found that blood plasma levels of $H_2S$ are low in patients that are obese.

In an embodiment, the patient is an elderly patient. In an embodiment, the patient is at least 50 years old, such as at least 55 years old, for example at least 60 years old.

In an embodiment, the patient has a body mass index (BMI) of at least 23 $kg/m^2$, such as a BMI of at least 25 $kg/m^2$, for example a BMI of at least 30 $kg/m^2$. The BMI is defined as the individual's body weight divided by the square of his or her height.

Any suitable mode of administration can be used to administer a compound comprising a mitochondrial targeting group linked to a group capable of releasing hydrogen sulfide to a human or animal, such as oral, rectal, vaginal, parenteral (e.g. intramuscular, intraperitoneal, intraarterial, intrathecal, intrabronchial, subcutaneous, intradermal, intravenous or intraarterial), nasal, buccal or sublingual routes of administration. The particular mode of administration and dosage regimen will be selected by the attending physician, taking into account a number of factors including the age, weight and condition of the patient.

A pharmaceutical composition comprising a compound which comprises a mitochondrial targeting group linked to a group capable of releasing hydrogen sulfide as an active principal will normally be formulated with an appropriate pharmaceutically acceptable excipient, carrier or diluent depending upon the particular mode of administration being used. For instance, parenteral formulations are usually injectable fluids that use pharmaceutically and physiologically acceptable fluids such as physiological saline or balanced salt solutions as a vehicle. Oral formulations, on the other hand, may be solids, e.g. tablets or capsules, or liquid solutions or suspensions.

The present invention provides a pharmaceutical composition comprising a compound which comprises a mitochondrial targeting group linked to a group capable of releasing hydrogen sulfide, or a pharmaceutically acceptable salt thereof, and a pharmaceutically acceptable excipient, diluent or carrier.

The pharmaceutical composition may be formulated in unit dosage form, i.e. in the form of discrete portions containing a unit dose, or a multiple or sub-unit of a unit dose. Suitable dosage forms include tablets, troches, dispersions, suspensions, solutions, capsules, creams, ointments and aerosols.

The amount of the compound comprising a mitochondrial targeting group linked to a group capable of releasing hydrogen sulfide that is given to a patient will depend upon the activity of the particular compound in question. Further factors include the condition being treated, the nature of the patient under treatment and the severity of the condition under treatment. The timing of administration of the compound should be determined by medical personnel, depending on the use. As a skilled physician will appreciate, and as with any drug, the compound may be toxic at very high doses.

The invention also relates to a combination comprising (i) a compound comprising a mitochondrial targeting group linked to a group capable of releasing hydrogen sulfide, or a pharmaceutically acceptable salt thereof, and (ii) an active agent suitable for use in the treatment of the human or animal body by surgery or therapy. The active agent suitable for use in the treatment of the human or animal body by surgery or therapy is different from the compound comprising a mitochondrial targeting group linked to a group capable of releasing hydrogen sulfide, or a pharmaceutically acceptable salt thereof.

In an embodiment, the active agent is for use in the treatment of a chronic inflammatory disease or disorder, an acute inflammatory disease or disorder, a disease or disorder associated with mitochondrial dysfunction, a disease or disorder associated with micro- or macro-angiopathy, a neurodegenerative disease, a disease or disorder associated with ageing, or a disease or disorder associated with organ failure, such as the diseases or disorders defined above.

Examples of suitable active agents include nifedipine and ritodrine.

The compounds comprising a mitochondrial targeting group linked to a group capable of releasing hydrogen sulfide may be given alone or in combination with one or more additional active agents useful for treating a disease or disorder susceptible to amelioration by in vivo release of hydrogen sulfide. Two or more compounds (i.e active agents) can be administered simultaneously, separately or sequentially. The active ingredients can be administered as a combined preparation.

Treatment of Plants

It has been found that compounds that are able to slowly release hydrogen sulfide in vivo are able to prevent stomatal closure in plants (M. Lisjak et al, Plant Physicol. Biochem., 2010, 48(12), 931-5). Mitochondria are present in plant cells, such as the guard cells that regulate the size of a stomatal opening. A compound comprising a mitochondrial targeting group linked to a group capable of releasing hydrogen sulfide can be used to prevent or reduce stomatal closure or to cause stomatal opening in a plant. The compound can be used to treat a plant to promote plant growth or to herbicidally treat a plant.

An aspect of the invention relates to plants, such as a plant or plants that has/have stomata. Stomata are present in the sporophyte generation of all land plant groups, except liverworts.

In an embodiment, the plant is a sporophyte generation of plant with the proviso that the plant is not a liverwort.

In an embodiment, the plant is a dicotyledon or a monocotyledon.

In an embodiment, the plant is a monocotyledon. Examples of suitable monocotyledon plants include grains (e.g. rice, wheat, maize, etc.), pasture grasses, sugar cane, bamboo, members of the palm family (Arecaceae), members of the banana family (Musaceae), members of the ginger family (Zingiberaceae), members of the onion family (Alliaceae), lilies, daffodils, irises, amaryllis, orchids, cannas, bluebells and tulips.

In an embodiment, the plant is a root crop (i.e. a plant that has an edible underground plant structure). Examples of suitable plants that are root crops include cassava, sweet potato, beet, carrot, rutabaga, turnip, parsnip, radish, yam, horseradish, sassafras, angelica, sarsaparilla and licorice.

In an embodiment, the plant is a member of the genus *Arabidopsis*.

In an embodiment, the plant is a member of the genus *Capsicum*.

In an embodiment, the plant is treated with the compound in an aqueous solution at a concentration of 0.5 µM to 250 µM, such as a concentration of 1 µM to 200 µM, for example 10 µM to 200 µM.

In an embodiment, the plant is treated with the compound in an aqueous solution at a concentration of 0.01 µM to 1500 µM, such as a concentration of 0.1 µM to 1000 µM.

In an embodiment, the plant is treated with the compound in an aqueous solution at a concentration of 10 nM to 450 nM, such as a concentration of 50 nM to 350 nM, for example 100 nM to 250 nM.

In an embodiment, the plant is treated with the compound simultaneously, concurrently, separately or sequentially with either (i) one or more plant nutrients, or (ii) one or more herbicides.

An aspect of the invention concerns treating a plant to promote plant growth. It may be necessary for the growth environment of the plant to be controlled to promote plant growth. For example, the growth environment may be controlled in a greenhouse or in a field. Generally, this may involve monitoring the environmental condition of the plant and supplying it with one or more plant nutrients as needed.

In an embodiment, the plant is grown indoors.

In an embodiment, the temperature, air humidity, moisture level of the soil, light intensity, light duration, the amount of $CO_2$ and/or the amount of plant nutrients fed to the plant are controlled when the growth environment of a plant is controlled.

It is known that plants have different photoperiods and respond differently to varying strengths of light intensity. The exact conditions of the growth environment and the amount of compound comprising a mitochondrial targeting group linked to a group capable of releasing hydrogen sulfide that are used to promote growth will depend on the specific plant that is to be treated. However, these may easily be determined by a person skilled in the art using commonly available techniques.

In an embodiment, the relative humidity of the growth environment is at least 60%, such as at least 75%, for example at least 80%.

In an embodiment, the average temperature of the growth environment is from 15 to 30° C., such as 18 to 25° C.

In an embodiment, the plant is treated with a compound comprising a mitochondrial targeting group linked to a group capable of releasing hydrogen sulfide under conditions where the amount of $CO_2$ is from 400 ppm to 1200 ppm, such as 450 ppm to 1000 ppm, for example 500 ppm to 800 ppm, or 550 ppm to 600 ppm. The amount of $CO_2$ in ppm generally refers to the amount of $CO_2$ in the air of the growth environment of the plant.

In the northern hemisphere, during the late autumn, winter and early spring, plants are generally exposed to relatively low levels of sunlight. It can be difficult to grow plants under such conditions without the aid of an artificial source of light, such as a grow lamp. The invention may allow plants to perform photosynthesis at relatively low levels of light and thereby to continue to grow, without the assistance of an artificial light source.

In an embodiment, the plant is treated with a compound comprising a mitochondrial targeting group linked to a group capable of releasing hydrogen sulfide under conditions where the light intensity is from 1 lux to 1000 lux, such as 5 lux to 500 lux, for example 50 lux to 250 lux.

The invention may promote plant growth by promoting plant transpiration, which usually occurs in the dark or under low levels of light.

In an embodiment, the plant is treated with a compound of the invention under conditions where the light intensity is from $10^{-4}$ lux to 0.5 lux, such as $10^{-3}$ lux to 0.25 lux, for example 0.01 to 0.1 lux.

The invention may also improve the growth of a plant during the daytime under conditions where there is plenty of light and the plant is adequately supplied with nutrients.

In an embodiment, the plant is treated with a compound comprising a mitochondrial targeting group linked to a group capable of releasing hydrogen sulfide under conditions where the light intensity is from 2000 lux to 5000 lux, such as 2500 lux to 4000 lux, for example 3000 lux to 3500 lux.

In an embodiment, the plant is exposed to 8 to 16 hours of light a day.

A compound comprising a mitochondrial targeting group linked to a group capable of releasing hydrogen sulfide may be used with one or more plant nutrients, which assist in promoting plant growth. Suitable plant nutrients are minerals or compounds that provide sources of nitrogen (e.g. nitrate), phosphorus (e.g. phosphate), potassium, calcium (e.g. lime), magnesium (e.g. lime), sulfur, iron, manganese, zinc, copper, boron, chlorine, and/or molybdenum. A fertilizer may include one or more of the plant nutrients.

Another aspect of the invention concerns a herbicidal treatment of a plant. When a plant is treated with a compound comprising a mitochondrial targeting group linked to a group capable of releasing hydrogen sulfide, its stomata may be prevented from closing. In hot and dry conditions, the plant will continue to transpire, such that it may dry out and die. The treatment may also allow pathogens to enter the plant through its stomata and cause disease, which may kill the plant.

In an embodiment, the plant is treated with a compound of the invention under conditions where the daytime temperature is an average of at 25° C., such as at least 30° C.

In an embodiment, the relative humidity of the plant environment is less than 50%, such as less than 40%, for example less than 30%, or less than 20%, or less than 10%.

In an embodiment, the plant is treated with a compound comprising a mitochondrial targeting group linked to a group capable of releasing hydrogen sulfide under conditions where the light intensity is at least 10,000 lux, such as at least 25,000 lux, for example at least 50,000 lux, or at least 100,000 lux, or at least 120,000 lux.

In an embodiment, the plant is a weed, such as *Ailanthus altissima*, Bermuda grass, bindweed, broadleaf plantain, burdock, clover, creeping Charlie, dandelion, goldenrod, Japanese knotweed, kudzu, leafy spurge, milk thistle, poison ivy, ragweed, sorrel, St John's wort, sumac, wild carrot, wood sorrel, common ragwort, spear thistle, creeping or field thistle, curled dock, broad leaved dock, chickweed, or barnyard grass.

A compound comprising a mitochondrial targeting group linked to a group capable of releasing hydrogen sulfide may be used with one or more herbicides. The compound may increase the efficacy of the herbicide by preventing a plant from closing its stomata.

In an embodiment, the herbicide is a post-emergent herbicide. Post-emergent herbicides are generally applied after a plant or crop has emerged.

Examples of suitable herbicides include acetochlor, acifluorfen, aclonifen, acrolein, alachlor, alloxydim, ametryn, amicarbazone, amidosulfuron, aminopyralid, amitrole, anilofos, asulam, atrazine, azimsulfuron, beflubtiamid, benazolin, benefin, bensulfuron, bensulide, bentazon, benzofenap, bifenox, bispyribac, bromacil, bromoxynil, butachlor, butafenacil, butroxydim, butylate, cacodylic acid, carbetamide, carfentrazone, chlorsulfuron, chlortoluron, cinmethylin, clethodim, clodinfop, clomazone, clopyralid, cloransulam-mezthyl, cyanazine, cycloate, cyclosulfamuron, cycloxydim, cyhalo fop, DCPA, 2,4-D, dazomet, desmedipham, desmetryn, dicamba, dichlobenil, dichlorprop, diclo fop, diclosulam, difenzoquat, diflufenican, diflufenzopyr, dimethenamid, diquat, dithiopyr, diuron, DSMA, endothall, EPTC, ethalfluralin, ethametsulfuron, ethofumesate, ethoxysulfuron, fenoxaprop, fentrazamide, flazasulfuron, florasulam, fluazifop-P, flucarbazone-sodium, flufenacet, flumetsulam, flumiclorac, flumioxazin, fluometuron, flupyrsulfuron, flurchloridone, fluridone, fluroxypyr, fluthiacet, foramsulfuron, fosamine, glufosinate, glyphosate, halosulfuron, haloxyfop, hexazinone, imazamethabenz, imazamox, imazapic, imazapyr, imazaquin, imazethapyr, iodosulfuron, isoxaben, isoxaflutole, lactofen, linuron, mecoprop, mefluidide, mesotrione, metham, metolachlor, metribuzin, metsulfuron, MSMA, napropamide, naptalam, nicosulfuron, norflurazon, oryzalin, oxadiazon, oxasulfuron, oxyfluorfen, paraquat, pebulate, pelargonic acid, pendimethalin, phenmedipham, picloram, picolinafen, pinoxaden, primisulfuron, prodiamine, prometon, prometryn, pronamide, propanil, propaquizafop, propoxycarbazone, prosulfocarb, propazine, prosulfuron, pyrazon, pyrasulfuron-ethyl, pyridate, pyrithiobac, pyrosulam, quinclorac, quinmerac, quizalofop, rimsulfuron, sethoxydim, siduron, simazine, sulcotrione, sulfentrazone, sulfometuron, sulfosulfuron, tebuthiuron, tepaloxydim, terbacil, terbutryn, thiazopyr, thifensulfuron, thiobencarb, topramezone, tralkoxydim, triallate, triasulfuron, tribenuron, triclopyr, trifloxysulfuron, trifluralin, triflusulfuron and vernolate.

The amount of the compound comprising a mitochondrial targeting group linked to a group capable of releasing hydrogen sulfide that is used to treat a plant will depend upon on the activity of the particular compound in question, the nature of the plant being treated and the desired effect. Further factors include the environmental conditions of the plant being treated. For example, high doses of the compound may be expected to have a herbicidal effect, particularly if the environmental conditions of the plant under treatment will not support enhanced plant growth. A person skilled in the art would readily be able to determine the amount of compound for achieving an effect in accordance with the use of the invention using rudimentary tests or standard tests that are well known in the art.

Definitions

It is to be understood that the wavy line in any chemical structures or moieties represented herein, such as shown below, indicates the point of attachment of that structure or moiety.

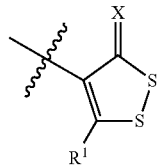

Any reference to groups or compounds for "releasing" or that are capable of "releasing" hydrogen sulfide as used herein refers to a group or a compound that undergoes a chemical reaction, e.g. in vivo, to produce $H_2S$, $HS^-$ and/or $S^{2-}$. In aqueous solution, $H_2S$ dissociates to form two dissociation states; the hydrosulfide anion (HS) and the sulfide anion ($S^{2-}$). The group or compound may therefore produce $H_2S$, $HS^-$ and/or $S^{2-}$, depending on the physiological conditions in the plant or animal.

The compounds comprising a mitochondrial targeting group linked to a group capable of releasing hydrogen sulfide may be present in the form of pharmaceutically acceptable salts. For use in medicines, the salts of the compounds refer to non-toxic "pharmaceutically acceptable salts". Examples of pharmaceutically acceptable salts are discussed in Berge et al (J. Pharm. Sci., 1977, 66, 1-19).

Pharmaceutically acceptable salt forms include pharmaceutically acceptable acidic/anionic or basic/cationic salts.

Examples of pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Examples of pharmaceutically acceptable basic/cationic salts include sodium, potassium, calcium, magnesium, diethanolamine, N-methyl-D-glucamine, L-lysine, L-arginine, ammonium, ethanolamine, piperazine and triethanolamine salts.

If the compound is anionic, or has a functional group which may be anionic, then a salt may be formed with a suitable cation. Examples of suitable inorganic cations include alkali metal ions, such as $Na^+$ and $K^+$, alkaline earth cations, such as $Ca^{2+}$ and $Mg^{2+}$, and other cations such as $Al^{3+}$. Examples of suitable organic cations include ammonium ion (i.e., $NH_4^+$) and substituted ammonium ions (e.g. $NH_3R^+$, $NH_2R_2^+$, $NHR_3^+$, $NR_4^+$, where R is an alkyl group).

If the compound is cationic, or has a functional group which may be cationic, then a salt may be formed with a suitable anion. Examples of suitable inorganic anions include those derived from the following inorganic acids: hydrochloric, hydrobromic, hydroiodic, sulfuric, sulfurous, nitric, nitrous, phosphoric, and phosphorous. Examples of suitable organic anions include those derived from the following organic acids: 2 acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric.

If the compound has both a cationic functional group, or a functional group that can become cationic, and an anionic functional group, or a functional group that can become anionic, then the compound may be present as a zwitterion.

The term "hydrogen" or "hydrogen atom" as used herein refers to a —H moiety.

The term "halogen" or "halogen atom" as used herein refers to a —F, —Cl, —Br or —I moiety.

The term "hydroxy" as used herein refers to a —OH moiety.

The term "alkyl" as used herein refers to a monovalent moiety obtained by removing a hydrogen atom from a carbon atom of a hydrocarbon compound having from 1 to 12 carbon atoms (unless otherwise specified), which may be aliphatic or alicyclic, and which may be saturated or unsaturated (e.g. partially unsaturated or fully unsaturated). Thus, the term "alkyl" includes the sub-classes alkenyl, alkynyl, cycloalkyl, cycloalkenyl and cylcoalkynyl below.

In the context of alkyl groups, the prefix $C_{1-12}$ denotes the number of carbon atoms, or range of number of carbon atoms present in that group. Thus, the term "$C_{1-12}$ alkyl" refers to an alkyl group having from 1 to 12 carbon atoms. The first prefix may vary according to the nature of the alkyl group. Thus, if the alkyl group is an alkenyl or alkynyl group, then the first prefix must be at least 2 (e.g. $C_{2-12}$). For cyclic (e.g. cycloalkyl, cycloalkenyl, cylcoalkynyl) or branched alkyl groups, the first prefix must be at least 3 (e.g. $C_{3-12}$).

Examples of saturated alkyl groups include methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$) and decyl ($C_{10}$). Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$). Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

The term "alkenyl" refers to an alkyl group having one or more carbon-carbon double bonds. Examples of unsaturated alkenyl groups include ethenyl (vinyl, —CH=CH$_2$), 1-propenyl (—CH=CH—CH$_3$) and 2-propenyl (allyl, —CH—CH=CH$_2$).

The term "alkynyl" refers to an alkyl group having one or more carbon-carbon triple bonds. Examples of unsaturated alkynyl groups include, but are not limited to, ethynyl (ethinyl, —C≡CH) and 2-propynyl (propargyl, —CH$_2$—C≡CH).

The term "cycloalkyl" refers an alkyl group which is also a cyclyl group; that is, a monovalent moiety obtained by removing a hydrogen atom from an alicyclic ring atom of a carbocyclic compound (i.e. a compound where all of the ring atoms are carbon atoms). The ring may be saturated or unsaturated (e.g. partially unsaturated or fully unsaturated), which moiety has from 3 to 12 carbon atoms (unless otherwise specified). Thus, the term "cycloalkyl" includes the sub-classes cycloalkenyl and cycloalkynyl. In an embodiment, each ring has from 3 to 7 ring carbon atoms. Examples of cycloalkyl groups include those derived from (i) saturated monocyclic hydrocarbon compounds: cyclopropane ($C_3$), cyclobutane ($C_4$), cyclopentane ($C_5$), cyclohexane ($C_6$), cycloheptane ($C_7$) and methylcyclopropane ($C_4$); (ii) unsaturated monocyclic hydrocarbon compounds: cyclopropene ($C_3$), cyclobutene ($C_4$), cyclopentene ($C_5$), cyclohexene ($C_6$), methylcyclopropene ($C_4$) and dimethylcyclopropene ($C_5$); (iii) saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin ($C_{10}$); (iv) unsaturated polycyclic hydrocarbon compounds: camphene ($C_{10}$), limonene ($C_{10}$), pinene ($C_{10}$); and (v) polycyclic hydrocarbon compounds having an aromatic ring: indene ($C_9$), indane ($C_9$) and tetraline ($C_{10}$).

In an embodiment, a reference to an alkyl group described herein is a $C_{1-12}$ alkyl group, such as a $C_{1-8}$ alkyl group, for example a $C_{1-6}$ alkyl group, or a $C_{1-4}$ alkyl group. The alkyl groups in the invention can be saturated alkyl groups or saturated cycloalkyl groups, for example saturated, unbranched alkyl groups.

The phrase "optionally substituted" as used herein refers to a parent group which may be unsubstituted or which may be substituted with a substituent.

The term "substituents" is used herein in the conventional sense and refers to a chemical moiety, which is covalently attached to, or if appropriate, fused to, a parent group.

The term "aryl" as used herein refers to a monovalent moiety obtained by removing a hydrogen atom from an aromatic ring atom of an aromatic compound, which moiety has from 6 to 10 ring carbon atoms (unless otherwise specified). In an embodiment, the aryl group is a phenyl group.

The term "alkoxy" used herein refers to an alkyl-oxy group, where the alkyl group is as defined above and has from 1 to 12 carbon atoms (unless otherwise specified). In an embodiment, the alkyl moiety in an alkoxy group is a saturated alkyl group or a saturated cycloalkyl group. In an embodiment, the alkyl moiety is a saturated, unbranched alkyl group. Examples of $C_{1-12}$ alkoxy groups include —OMe (methoxy), —OEt (ethoxy), —O($^n$Pr) (n-propoxy), —O($^i$Pr) (isopropoxy), —O($^n$Bu) (n-butoxy), —O($^s$Bu) (sec-butoxy), —O($^i$Bu) (isobutoxy), and —O($^t$Bu) (tert-butoxy).

The term "alkylene" as used herein refers to a bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene as discussed below. The prefix (e.g. $C_{1-4}$, $C_{1-7}$, $C_{1-20}$) denotes the number of carbon atoms, or a range for the number of carbon atoms. For example, the term "$C_{1-20}$alkylene" used herein, refers to an alkylene group having from 1 to 20 carbon atoms.

Examples of linear saturated $C_{1-20}$alkylene groups include —(CH$_2$)— where n is an integer from 1 to 20, such as —CH$_2$— (methylene), —CH$_2$CH$_2$— (ethylene), —CH$_2$CH$_2$CH$_2$— (propylene), and —CH$_2$CH$_2$CH$_2$CH$_2$— (butylene). Examples of branched saturated $C_{1-20}$alkylene groups include —CH(CH$_3$)—, —CH(CH$_3$)CH$_2$—, and —CH(CH$_3$)CH$_2$CH$_2$—. Examples of linear partially unsaturated $C_{2-20}$alkylene groups include —CH=CH— (vinylene), —CH=CHCH$_2$—, —CH$_2$—CH=CH$_2$—, and —CH=CHCH$_2$CH$_2$—. Examples of branched partially unsaturated $C_{1-20}$alkylene groups include —C(CH$_3$)=CH—, —C(CH$_3$)=CHCH$_2$— and —CH=CHCH(CH$_3$)—. Examples of alicyclic saturated $C_{3-20}$alkylene groups include cyclopentylene (e.g. cyclopent-1,3-ylene) and cyclohexylene (e.g. cyclohex 1,4 ylene). Examples of alicyclic partially unsaturated $C_{2-20}$alkylene groups include cyclopentenylene (e.g. 4-cyclopenten-1,3-ylene), cyclohexenylene (e.g. 2 cyclohexen-1,4-ylene; 3 cyclohexen-1,2-ylene; 2,5 cyclohexadien-1,4-ylene).

In an embodiment, a reference to an alkylene group described herein is a $C_1$-20alkylene group, such as a $C_{1-12}$alkylene group, for example a $C_{2-8}$alkylene group, or a $C_{3-7}$alkylene group. In an embodiment, the alkylene groups can be saturated alkyl groups or saturated cycloalkyl groups, such as saturated, unbranched alkyl groups (i.e. straight chain alkylene group).

The term "arylene" as used herein refers to a bidentate moiety obtained by removing two hydrogen atoms, one from each of two different aromatic ring atoms of an aromatic compound, which moiety has from 6 to 10 ring atoms (unless otherwise specified). In an embodiment, each ring has from 6 to 8 ring atoms. In this context, the prefix (e.g. $C_{6-10}$) denotes the number of ring atoms, or a range for the number of ring carbon atoms.

In some embodiments, substituents can themselves be substituted. For example, a $C_{1-12}$alkyl group may be substituted with, for example, hydroxy (referred to as a hydroxy-$C_{1-12}$alkyl group) or a halogen atom (referred to as a halo-$C_{1-12}$alkyl group), and a $C_{1-12}$alkoxy group may be substituted with, for example, a halogen atom (referred to as a halo-$C_{1-12}$alkoxy group).

The term "alkylene-arylene" used herein refers to a bidentate moiety comprising an alkylene moiety, -alkylene-, linked to an arylene moiety, -arylene-, that is, -alkylene-arylene-. Examples of alkylene-arylene groups include $C_{1-20}$alkylene-$C_{6-10}$arylene, such as methylene-phenylene, ethylene-phenylene, propylene-phenylene, and ethenylene-phenylene (also known as vinylene-phenylene).

The term "phosphinodithioate" as used herein refers to a >P(S)S$^-$ group.

The term "phosphinodithioic acid" as used herein refers to a >P(S)SH group.

Certain compounds may exist in one or more particular geometric, enantiomeric, diasteriomeric, tautomeric, or conformational forms. Unless otherwise specified, a reference to a particular compound includes all such isomeric forms, including (wholly or partially) racemic and other mixtures thereof. Methods for the preparation and separation of such isomeric forms are either known in the art.

Any reference to "promote plant growth" as used herein refers to an increase in the dry weight of an individual plant or an increase in crop yield compared to that which would be obtained without using a compound of the invention under otherwise identical conditions.

The term "treatment" in the context of treating plants as used herein refers to the application of a compound or composition of the invention to a plant, such as by spraying a solution or composition of the invention over or around the plant.

Any reference to an "increase in efficacy of a herbicide" as used herein refers to an increase in the herbicidal effectiveness of the herbicide. Thus, a larger number of plants may be killed when the herbicide is used with a compound of the invention compared to that which would be obtained without using a compound of the invention under otherwise identical conditions. Alternatively, the amount or concentration of the herbicide that is used to kill a specific number or quantity of plants will be lower when used with a compound of the invention, compared to the amount or concentration of herbicide that would be used without using a compound of the invention under otherwise identical conditions.

The invention will now be illustrated by the following, non-limiting examples.

Example 1

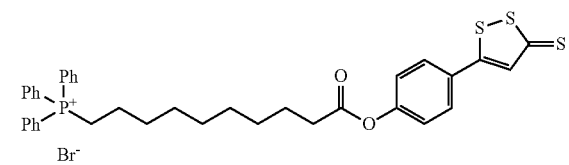 [SMILES: O=C(CCCCCCCCC[P+](c1ccccc1)(c1ccccc1)c1ccccc1)Oc1ccc(-c2cc(=S)ss2)cc1 ; [Br-]]

[AP39]

Synthesis of AP39

A solution of 10-bromodecanoic acid (500 mg, 1.99 mmol) in acetonitrile (5 mL) was added to a stirred solution of triphenylphosphine (522 mg, 1.99 mmol) in acetonitrile (5 mL). The solution was heated at reflux for 70 h, cooled to room temperature then concentrated in vacuo. The resulting material was washed with toluene (2×10 mL), concentrated in vacuo then dissolved in dichloromethane (30 mL). To this stirred solution was added 5-p-hydroxyphenyl-1,2-dithiole-3-thione (ADT-OH) (456 mg, 1.99 mmol), N,N'-dicyclohexylcarbodiimide (431 mg, 2.09 mmol) and 4-dimethylaminopyridine (12 mg, 0.0995 mmol). After 22 h, the resulting suspension was filtered through cotton wool and the filtrate was concentrated in vacuo. Purification by flash column chromatography, loading as a dichloromethane solution and eluting with ethyl acetate then methanol, gave a mixture of the phosphonium salt and silica. Redissolution in dichloromethane, filtration through paper and concentration in vacuo gave the pure phosphonium salt (1.05 g, 73%) as an orange foam.

$R_f$=0.7 (methanol); $^1$H NMR (300 MHz, CDCl$_3$): δ=7.95-7.65 (m, 17H; 3×Ph and Ar 2- and 6-H), 7.42 (s, 1H; =CH), 7.23 (d, J=8.0 Hz, 2H; Ar 3- and 5-H), 3.90-3.79 (m, 2H; CH$_2$C=O), 2.58 (t, J=8.5 Hz, 2H; CH$_2$P), 1.80-1.55 (m, 4H; 2×CH$_2$), 1.42-1.19 ppm (m, 10H; 5×CH$_2$); $^{31}$P NMR (121 MHz, CDCl$_3$): δ=25.7 ppm; HRMS (ESI) calculated for C$_{37}$H$_{38}$O$_2$PS$_3$ [M—Br]$^+$ requires 641.1766. found 641.1751.

ADT-OH can be prepared using the method described in US 2008/0004245.

Example 2

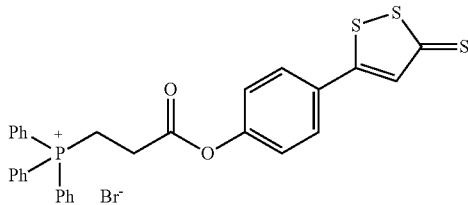

The method of Example 1 was used, except 3-bromopropionic acid (153 mg, 1.00 mmol) was used instead of 10-bromodecanoic acid. A phosphonium salt (482 mg, 77%) was obtained as an orange foam.

$R_f$=0.7 (methanol); $^1$H NMR (300 MHz, CDCl$_3$): δ=7.96-7.60 (m, 17H; 3×Ph and Ar 2- and 6-H), 7.36 (s, 1H; =CH), 7.18 (d, J=8.0 Hz, 2H; Ar 3- and 5-H), 4.49-4.36 (m, 2H; CH$_2$C=O), 3.40-3.26 ppm (m, 2H; CH$_2$P).

Example 3

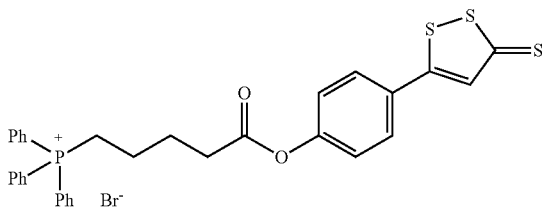

The method of Example 1 was used, except 5-bromovaleric acid (181 mg, 1.00 mmol) was used instead of 10-bromodecanoic acid. A phosphonium salt (396 mg, 61%) was obtained as an orange foam.

$R_f$=0.8 (methanol); $^1$H NMR (300 MHz, CDCl$_3$): δ=7.93-7.65 (m, 17H; 3×Ph and Ar 2- and 6-H), 7.41 (s, 1H; =CH), 7.21 (d, J=8.0 Hz, 2H; Ar 3- and 5-H), 4.11-3.99 (m, 2H; CH$_2$C=O), 2.81 (t, J=8.5 Hz, 2H; CH$_2$P), 2.22-2.12 (m, 2H; CH$_2$), 1.90-1.77 ppm (m, 2H; CH$_2$).

Example 4

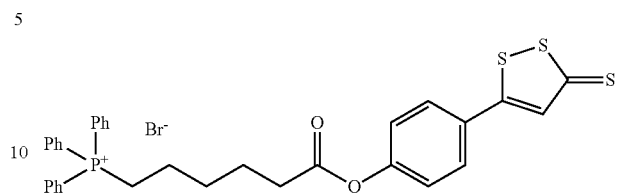

The method of Example 1 was used, except 6-bromohexanoic acid (195 mg, 1.00 mmol) was used instead of 10-bromodecanoic acid. A phosphonium salt (447 mg, 67%) was obtained as an orange foam.

$R_f$=0.8 (methanol); $^1$H NMR (300 MHz, CDCl$_3$): δ=7.85-7.59 (m, 17H; 3×Ph and Ar 2- and 6-H), 7.32 (s, 1H; =CH), 7.18 (d, J=8.0 Hz, 2H; Ar 3- and 5-H), 3.85-3.70 (m, 2H; CH$_2$C=O), 2.56 (t, J=8.5 Hz, 2H; CH$_2$P), 1.87-1.52 ppm (m, 6H; 3×CH$_2$).

Example 5

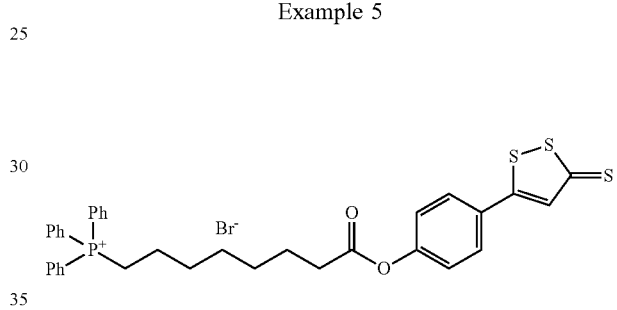

The method of Example 1 was used, except 8-bromooctanoic acid (223 mg, 1.00 mmol) was used instead of 10-bromodecanoic acid. A phosphonium salt (529 mg, 76%) was obtained as an orange foam.

$R_f$=0.8 (methanol); $^1$H NMR (300 MHz, CDCl$_3$): δ=7.95-7.67 (m, 17H; 3×Ph and Ar 2- and 6-H), 7.42 (s, 1H; =CH), 7.22 (d, J=8.0 Hz, 2H; Ar 3- and 5-H), 3.97-3.88 (m, 2H; CH$_2$C=O), 2.58 (t, J=8.5 Hz, 2H; CH$_2$P), 1.80-1.52 (m, 4H; 2×CH$_2$), 1.45-1.32 ppm (m, 6H; 3×CH$_2$); $^{31}$P NMR (121 MHz, CDCl$_3$): δ=29.2 ppm.

Example 6

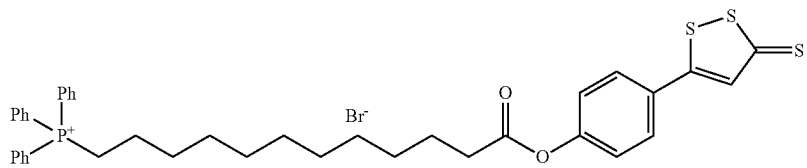 [SMILES: O=C(CCCCCCCCCCC[P+](c1ccccc1)(c1ccccc1)c1ccccc1)Oc1ccc(-c2cc(=S)ss2)cc1 ; [Br-]]

The method of Example 1 was used, except 12-bromododecanoic acid (279 mg, 1.00 mmol) was used instead of 10-bromodecanoic acid. A phosphonium salt (503 mg, 67%) was obtained as an orange foam.

$R_f$=0.7 (methanol); $^1$H NMR (300 MHz, CDCl$_3$): δ=7.95-7.68 (m, 17H; 3×Ph and Ar 2- and 6-H), 7.40 (s, 1H; =CH), 7.21 (d, J=8.0 Hz, 2H; Ar 3- and 5-H), 3.91-3.79 (m, 2H; CH$_2$C=O), 2.60 (t, J=8.5 Hz, 2H; CH$_2$P), 1.82-1.61 (m, 4H; 2×CH$_2$), 1.45-1.15 ppm (m, 14H; 7×CH$_2$).

Example 7

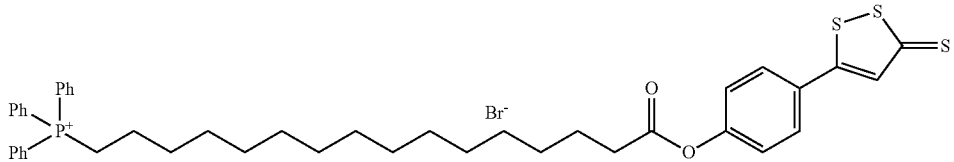 [SMILES: O=C(CCCCCCCCCCCCCCC[P+](c1ccccc1)(c1ccccc1)c1ccccc1)Oc1ccc(-c2cc(=S)ss2)cc1 ; [Br-]]

The method of Example 1 was used, except 16-bromohexadecanoic acid (335 mg, 1.00 mmol) was used instead of 10-bromodecanoic acid. A phosphonium salt (334 mg, 41%) was obtained as an orange foam.

$R_f$=0.7 (methanol); $^1$H NMR (300 MHz, CDCl$_3$): δ=7.97-7.65 (m, 17H; 3×Ph and Ar 2- and 6-H), 7.39 (s, 1H; =CH), 7.22 (d, J=8.0 Hz, 2H; Ar 3- and 5-H), 3.90-3.75 (m, 2H; CH$_2$C=O), 2.61 (t, J=8.5 Hz, 2H; CH$_2$P), 1.80-1.55 (m, 4H; 2×CH$_2$), 1.47-1.11 ppm (m, 22H; 11×CH$_2$).

Example 8

[AP123]

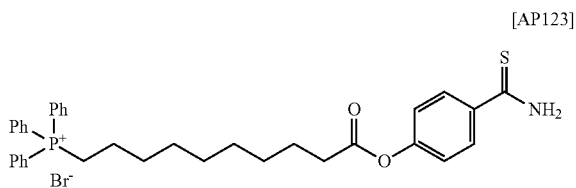 [SMILES: NC(=S)c1ccc(OC(=O)CCCCCCCCC[P+](c2ccccc2)(c2ccccc2)c2ccccc2)cc1 ; [Br-]]

Synthesis of AP123

The method of Example 1 was used, except 4-hydroxythiobenzamide (123 mg, 0.803 mmol) was used instead of ADT-OH. A phosphonium salt (208 mg, 40%) was obtained as an orange foam.

$R_f$=0.4 (methanol); $^1$H NMR (300 MHz, CDCl$_3$): δ=8.15 (d, J=8.5 Hz, 2H; Ar 2- and 6-H), 7.85-7.60 (m, 15H; 3×Ph), 6.96 (d, J=8.5 Hz, 2H; Ar 3- and 5-H), 3.51-3.38 (m, 2H; CH$_2$C=O), 2.58-2.41 (m, 2H; CH$_2$P), 1.72-1.55 (m, 4H; 2×CH$_2$), 1.42-1.13 ppm (m, 10H; 5×CH$_2$); $^{31}$P NMR (121 MHz, CDCl$_3$): δ=25.1 ppm.

Experimental Methods and Results

H$_2$S Generation Assay

Generation of H$_2$S from AP39 and AP123 was determined by zinc-trap spectrophotometry, such as described by B. Fox et al (Fox, B., Schantz, J-T., Haigh, R., Wood, M. E., Moore, P. K., Viner, N., Spencer, J. P., Winyard, P. G. & Whiteman, M.; "Inducible hydrogen sulfide synthesis in chondrocytes and mesenchymal progenitor cells: Is H$_2$S a novel cytoprotective mediator in the inflamed joint?", J. Cell. Mol. Med., 2011, In Press).

A 200 µl solution of AP39 or AP123 was added to phosphate buffer (pH 7.4, 25° C.) in sealed Eppendorf tubes for one hour. After this time, 250 µl of zinc acetate (1% w/v) was added followed by 133 µL N,N-dimethyl-p-phenylenediamine sulfate (20 mM) and 133 µL FeCl$_3$ (30 mM). After incubation at room temperature in the dark for 60 mins absorbance (670 nm) determined using a Gemini M2e microplate reader. The H$_2$S concentration of each sample was calculated against a calibration curve of Na$_2$S. The results are shown in FIG. 1.

Cell Death Assays

Initial experiments were conducted to determine whether the H$_2$S donor compounds were toxic. Human brain microvascular endothelial cells (HMEC) were incubated with increasing concentrations of a H$_2$S donor compound for 24 hours. After this time cell viability was assessed by an Alamar Blue assay. Fluorescence (excitation wavelength 540 nm, emission wavelength 612 nm) was detected using a Gemini M2e microplate reader. The method was performed in accordance with the method described by D. Vauzour et al (J. Agric. Food Chem., 2007, 55 (8), 2854-2860).

Prevention of Cell Death Induced by Oxidants

HMEC were incubated for 5 hrs with H$_2$S donor compounds then oxidants added for 24 hrs. After this time cell viability (survival) was assessed by an Alamar Blue assay. 3-morpholinosydnonimine hydrochloride (SIN-1) was used to generate a flux of peroxynitrite (ONOO$^-$), hydrogen peroxide (H$_2$O$_2$) and the lipid peroxide 4-hydroxynonenal (HNE) to induce oxidative stress and cell death. The method was performed in accordance with the method described by D. Vauzour et al (J. Agric. Food Chem., 2007, 55 (8), 2854-2860).

Intracellular Oxidative Stress Measurements

HMEC were incubated with H$_2$S donor compounds for 5 hrs then H$_2$O$_2$, FINE or SIN-1 were added for 2 hrs. Intracellular oxidative stress was then assessed using dichlorofluorescein diacetate (added at a final concentration of 10 µM) and fluorescence detected using a Gemini M2e microplate reader at 37° C. (excitation wavelength, 488 nm, emission wavelength 525 nm). The method was performed in accordance with the method described by M. Whiteman et al (Meths. Mol. Biol., 2008, 476, 29-50).

Mitochondrial Oxidative Stress Measurements

HMEC were incubated with H$_2$S donor compounds for 5 hrs then the oxidants H$_2$O$_2$, SIN-1 or FINE added for 2 hrs. We used a mitochondria-selective oxidant probe MitoSox Red (final concentration, 5 µM) to detect mitochondria-derived oxidant species by fluorescence using a Gemini M2e microplate reader (excitation wavelength 510 nm, emission wavelength, 580 nm). The method was performed in accordance with the method described by M. Whiteman et al (Meths. Mol. Biol., 2008, 476, 29-50) and R. A. Quintanilla et al (J Biol Chem., 2008, 284, 18754-18766).

Mitochondrial Membrane Potential (ΔΨm)

HMEC were incubated with H$_2$S donor compounds for 5 hrs followed by the addition of oxidants SIN-1 (500 µM), H$_2$O$_2$ (50 µM) or FINE (10 µM) for 24 hrs. After this time the mitochondria-specific potentiometric dye tetramethylrhodamine methyl ester (200 nM) was added and fluorescence was determined using a Gemini M2e microplate reader (excitation wavelength 548 nm, emission wavelength 573 nm). The method was performed in accordance with the method described by M. Whiteman et al (FASEB J, 2004, 18, 1395-1397).

Measurements of Effect of AP39 on Rat Blood Pressure, Heart Rate and Breathing Rate (In Vivo)

Hydrogen sulfide donor molecules are of potential therapeutic value in the management of cardiovascular pathologies. However, their molecular mechanism is not fully understood.

The aim of this study was to compare the pharmacological effects of the fast $H_2S$ release drug $Na_2S$ and a novel slow release $H_2S$ compound AP39 in the rat vasculature; particularly, blood pressure, heart rate (in vivo) and breathing rate. To look for the molecular mechanism of the effects we studied the influence of AP39 on vessel reactivity using aortic ring organ baths (ex vivo) (see "Measurements of effect of AP39 on relaxation of adrenaline pre-contracted rat aortic rings" below) and the effects of AP39 on single channel properties of chloride channels derived from rat heart sarcoplasmic reticulum (see "Measurements of AP39 on single channel properties of chloride channels derived from rat heart sarcoplasmic reticulum" below).

The mean arterial blood pressure (MAP) of anaesthetised Wistar rats was measured by a pressure transducer in the carotid artery. In ex vivo experiments, effects of AP39 were studied on noradrenaline precontracted rat aortic rings (see below). The single channel properties of intracellular chloride channels from rat heart were studied using the bilayer lipid membrane method (see below).

Figure 20:
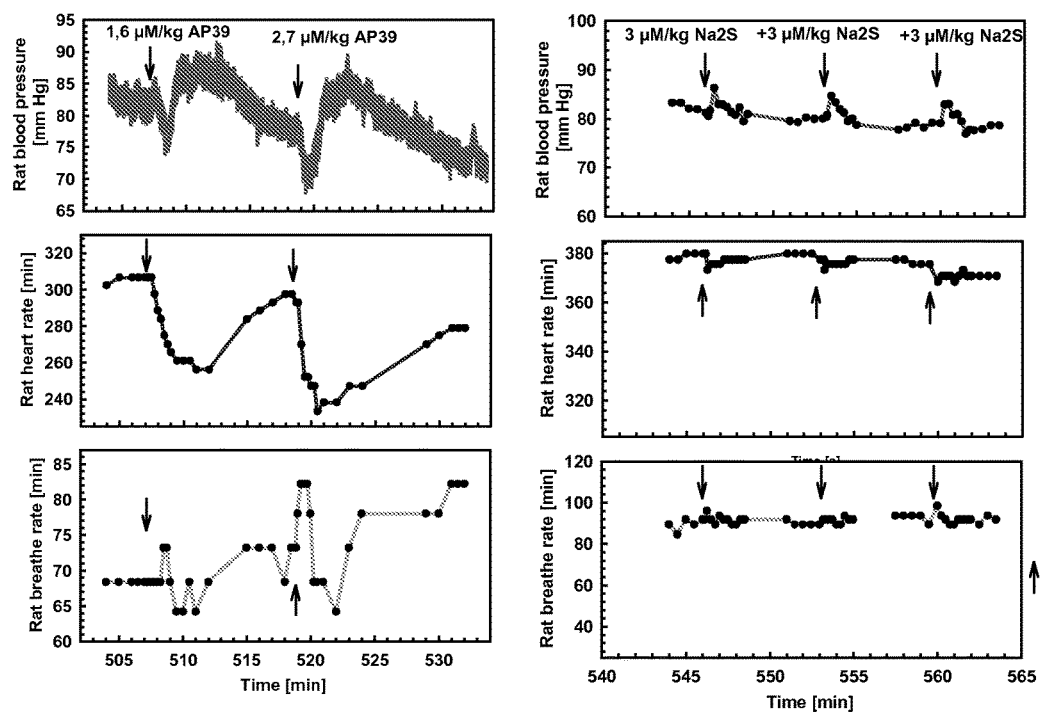
FIG. 20 is a set of graphs which show a comparison of the effects of $H_2S$ release drugs AP39 and $Na_2S$, respectively, on blood pressure, heart rate and breathing rate of an anesthetised Wistar rat.
Figure 21:
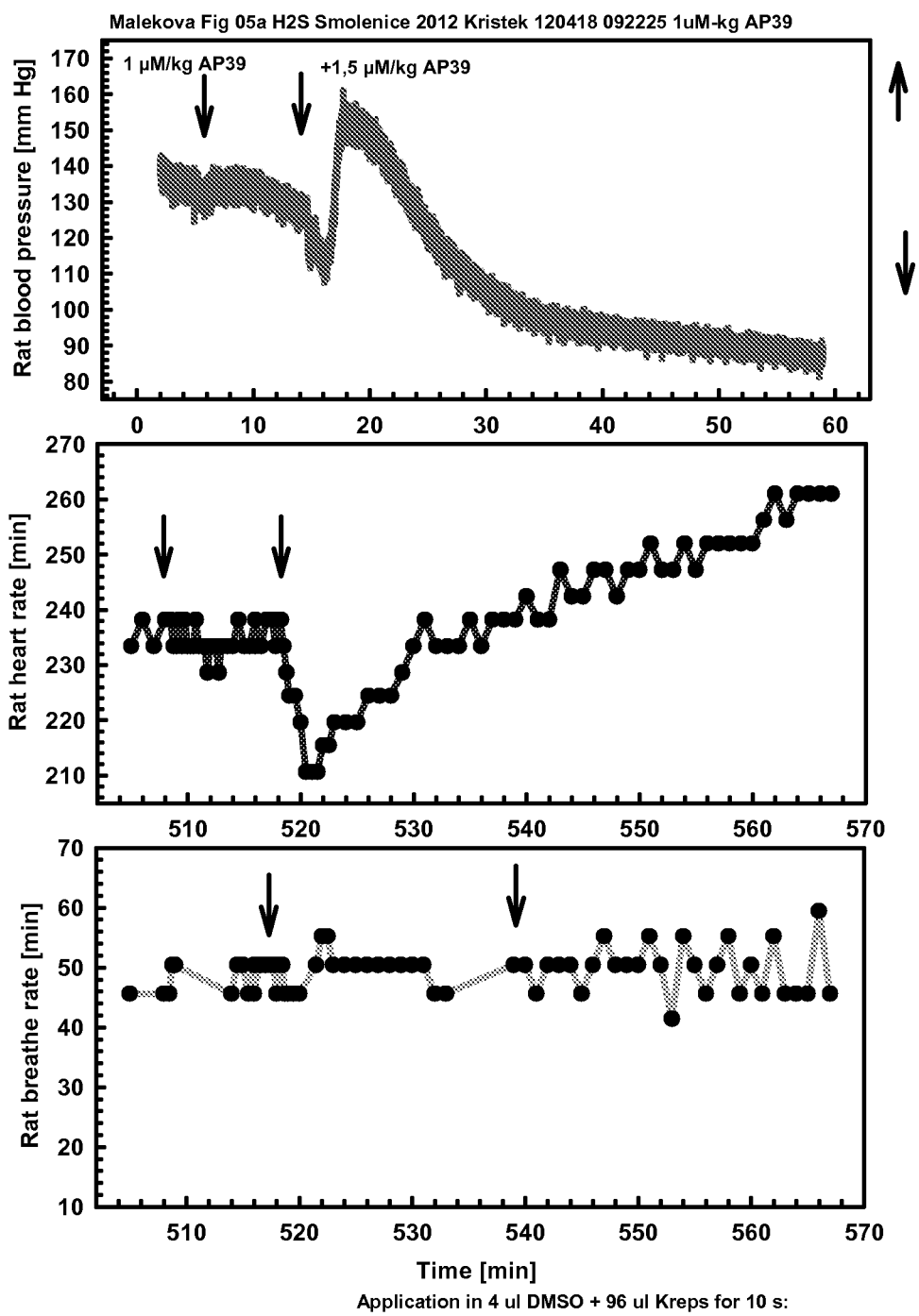
FIG. 21 is a set of graphs which show the effect of AP39 on blood pressure, heart rate and breathing rate of an anesthetised SHR (1 year old 450 g) rat.
Figure 22:
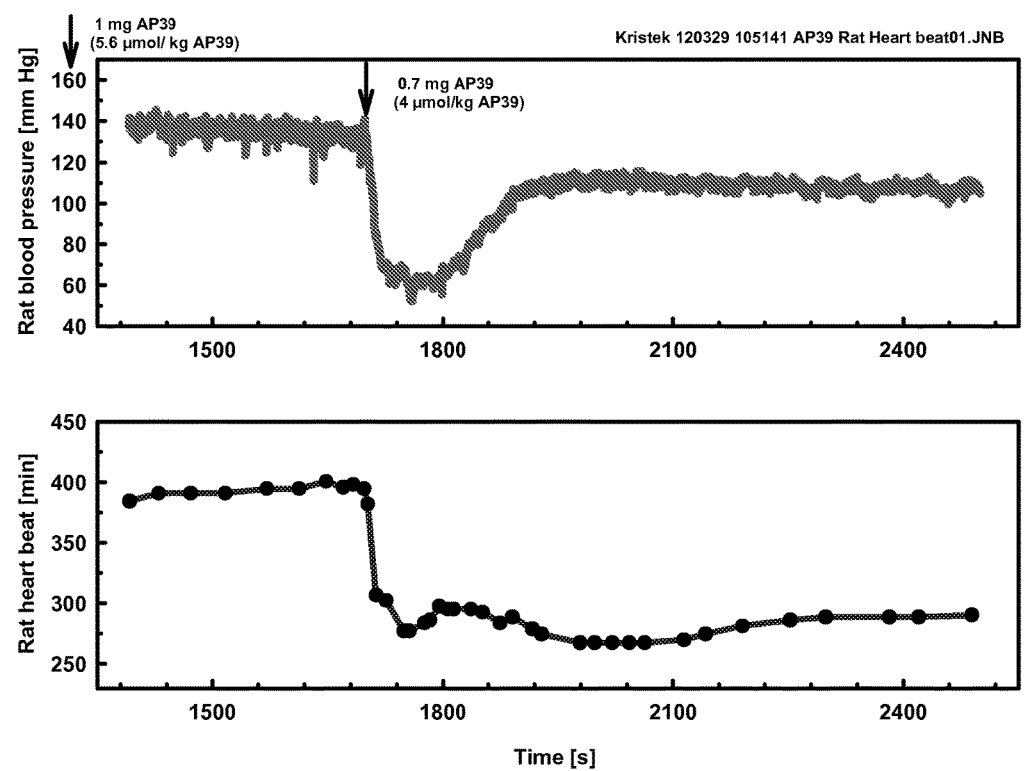
FIG. 22 is a set of graphs which shows the effect of AP39 on blood pressure and heart rate of an anesthetised Wistar rat at a higher concentration of AP39 than in FIG. 20

The catheter was inserted into the right jugular vein of male wistar rats or male spontaneously hypertensive (SHR) rats so as to reach the right atrium. Anesthesia (ZOLELIT, VIRBAC, 40 mg/kg to leg) and Xylazine 2%. AP39 solutions were prepared in 4 µl DMSO then mixed with 100 µl Krebs solution and immediately applied for 10 sec. (FIGS. 20, 21 and 22).

Blood pressure, heart rate and breathing rate were all measured at the same time, in accordance with Ling et al., 2008 Circulation 117 2351-2360.

Figure 23:
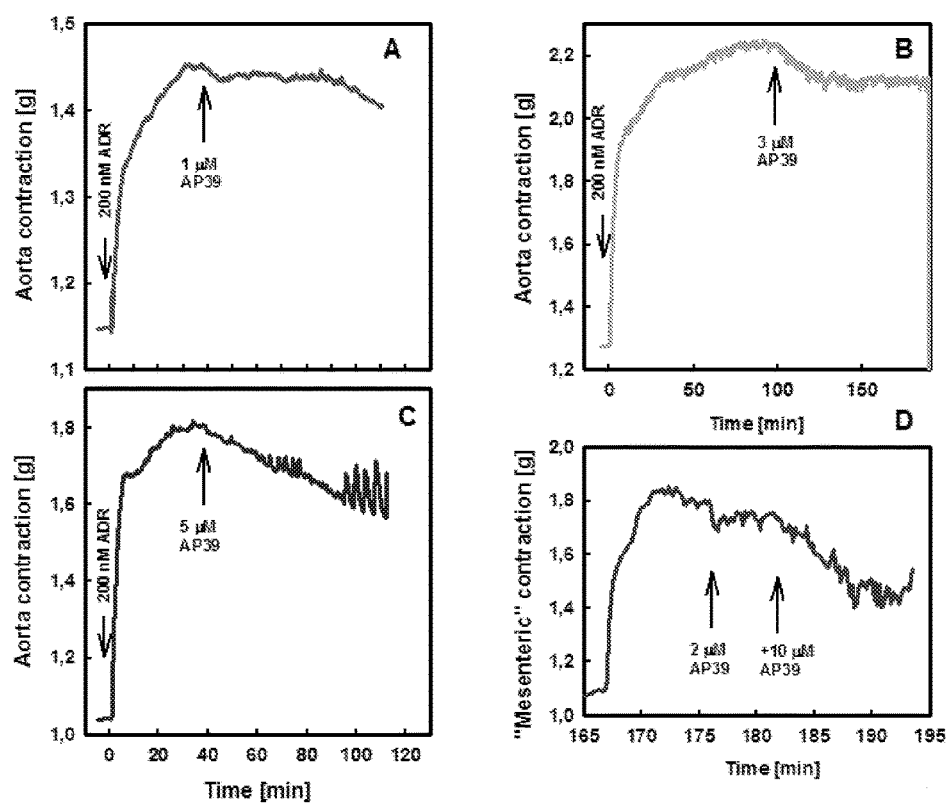
FIG. 23 is a set of graphs which show the vasodilatory effects of increasing concentrations of AP39 (1-5 μM) on adrenaline-precontracted rat aorta (A-C) and mesenteric arteries (D).

Measurements of Effect of AP39 on Relaxation of Adrenaline Precontracted Rat Aortic Rings The rings of thoracic aorta (approx. 3-4-mm diameter) or mesenteric artery were prepared from male Wistar rats and were mounted for recording of isometric tension changes in pneumoxid-oxygenated (95% $O_2$:$CO_2$, 37° C.) Krebs-bicarbonate solution as described in Ling et al., 2008 Circulation 117 2351-2310. The aortic ring was pre-contracted with 200 nmol/l adrenaline and the effect of AP39 was evaluated (FIG. 23).

Measurements of Effect of AP39 on Single Channel Properties of Chloride Channels Derived From Rat Heart Sarcoplasmic Reticulum Chloride channels play a role in blood pressure regulation, cell cycle, apoptosis, muscle tone, volume regulation, synaptic transmission, and cellular excitability.

Sarcoplasmic reticulum (SR) vesicles, isolated from rat heart, were fused into bilayer lipid membrane separating the cis and trans chambers, and electrical current through the single chloride channel was measured. The composition of the solutions (in mM) was: trans: 50 KCl, 1 $MgCl_2$, 0.1 $CaCl_2$, 0.3 EGTA, 10/5 Hepes/Tris, 7.4 pH (~luminal side), and cis: 250 KCl, 1 $MgCl_2$, 0.3 $CaCl_2$, 10/5 Hepes/Tris, 7.4 pH (~cytoplasmic side).

The single channel parameters: Open probability, current-voltage relationship, reversal potential, mean open and close time and single current amplitude were evaluated (FIGS. 24-28).

Measurements of the Effect of AP39 on T-Type Calcium Channel CAv3.1

CAv3.1 calcium channels were permanently transfected in human embryonic kidney (HEK 293) cells and the calcium currents were measured by a patch-clamp method in the whole cell configuration, from a holding potential −100 mV.

Figure 29:
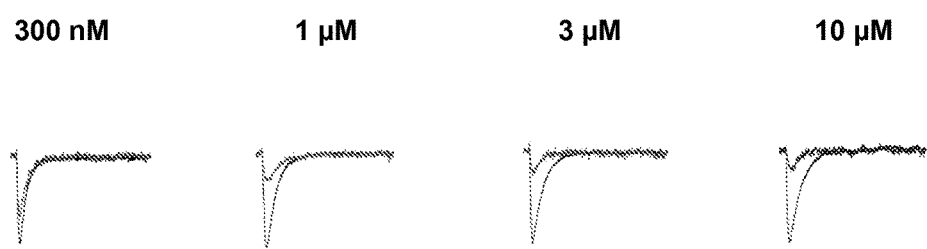
FIG. 29 is a set of graphs which show the effect of AP39 on CAv3.1 T-type calcium channels in human embryonic kidney (HEK293) cells in a concentration dependent manner.
Figure 30:
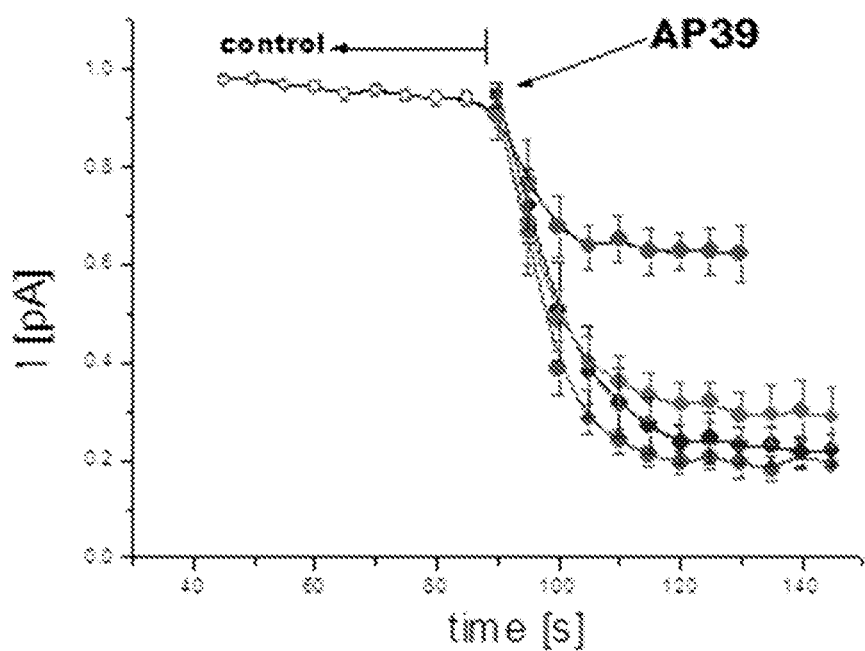
FIG. 30 is a set of graphs which show the effect of AP39 on CAv3.1 T-type calcium channels in human embryonic kidney (HEK293) cells in a time dependent manner.
Figure 31:
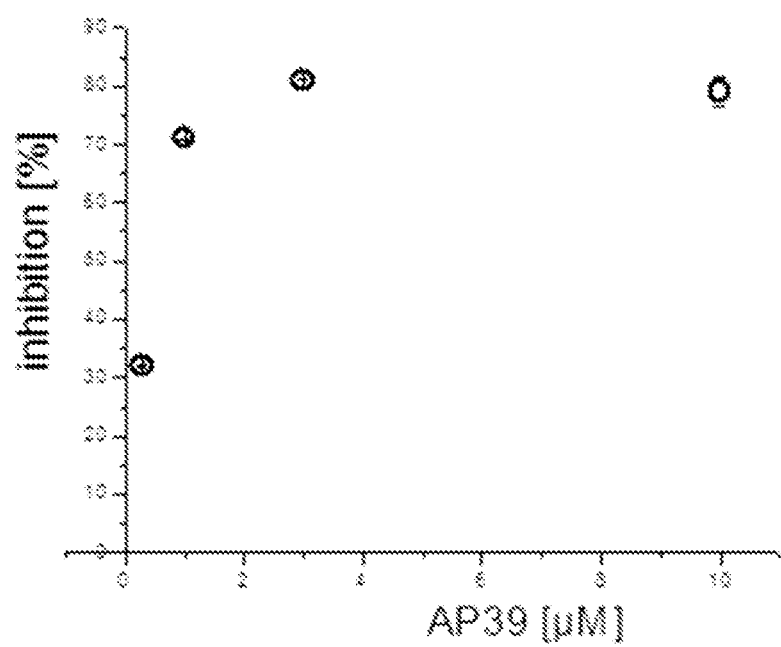
FIG. 31 is a set of graphs which show the effect of AP39 on CAv3.1 T-type calcium channels in human embryonic kidney (HEK293) cells in a concentration dependent manner.

The effect of four different concentrations of AP39 on the current through a Cav3.1 channel was tested (FIGS. 29-31).
Western Blot Analysis of Mitochondria Specific Proteins Human THP-1 (monocytic) cells were exposed to an oxidative stress inducing agent (hydrogen peroxide; $H_2O_2$, 25 µM) in the presence or absence of the mitochondria-targeted $H_2S$ donor AP39.

Figure 32:
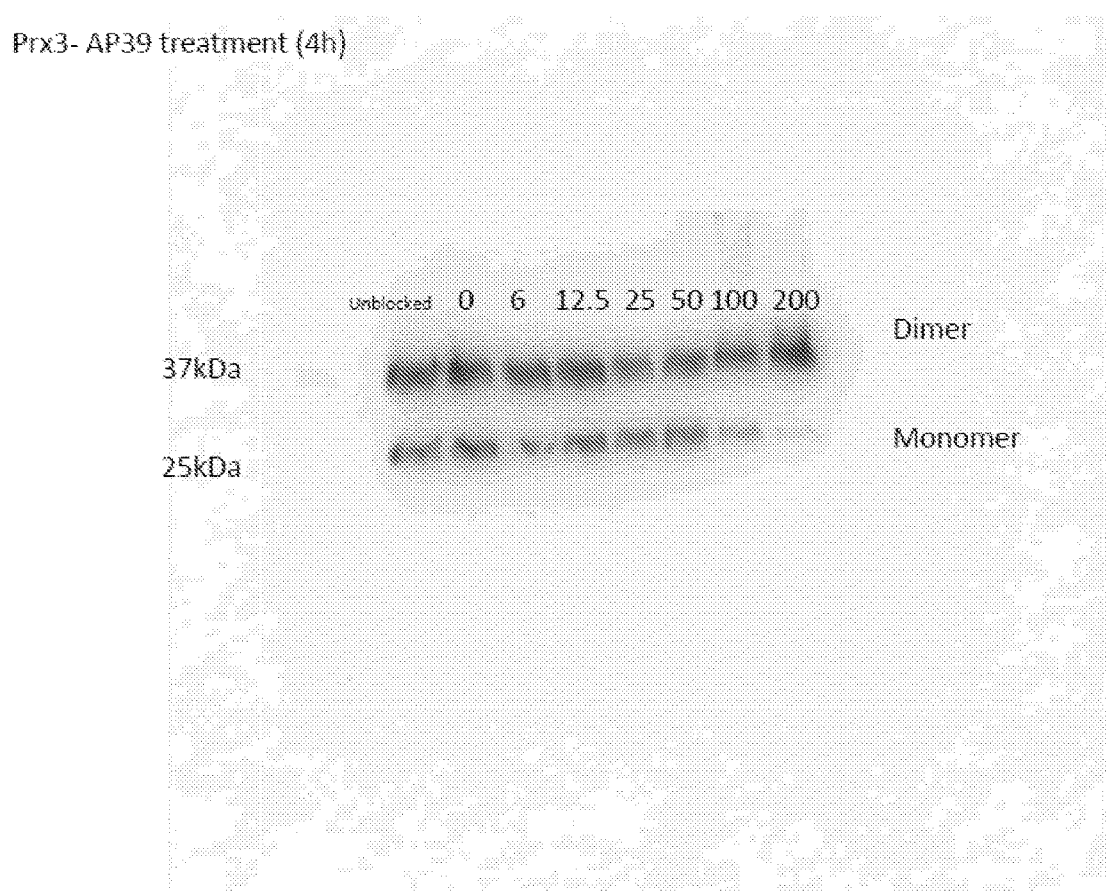
FIG. 32 is a western blot showing the inhibition of hydrogen peroxide-induced oxidation of enzyme peroxiredoxin 3 (Prx3), located in the mitochondrial matrix, by different concentrations of AP39 in human THP-1 (monocyte) cells.

In the experiment resulting in FIG. 32, the human THP-1 (monocytic) cells were exposed to 25 µM $H_2O_2$ for 4 hours in the absence or presence of different concentrations of AP39 (given in µM).

Figure 33:
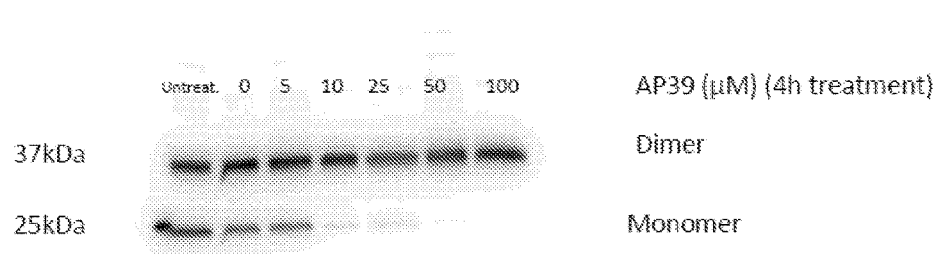
FIG. 33 is a western blot showing the inhibition of hydrogen peroxide-induced oxidation of enzyme peroxiredoxin 3 (Prx3), located in the mitochondrial matrix, by different concentrations of AP39 in human THP-1 (monocyte) cells.

In the experiment resulting in FIG. 33, the human THP-1 (monocytic) cells were exposed to different concentrations of AP39 (given in µM) for 4 hours followed by the addition of 25 µM $H_2O_2$ for 1 minute.

Figure 34:
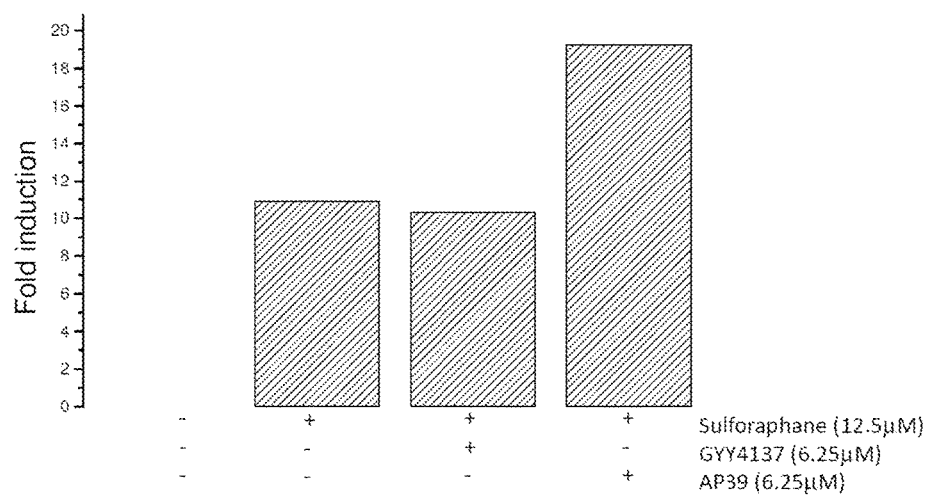
FIG. 34 is a graph showing the activation of the transcription factor Nrf2 by AP39 in Nrf2-luciferase transfected MCF-7 cells (AREc32). The figure also compares the effects of non-mitochondria targeted slow release $H_2S$ donor compound GYY4137 and a positive control (sulforaphane).
Figure 35:
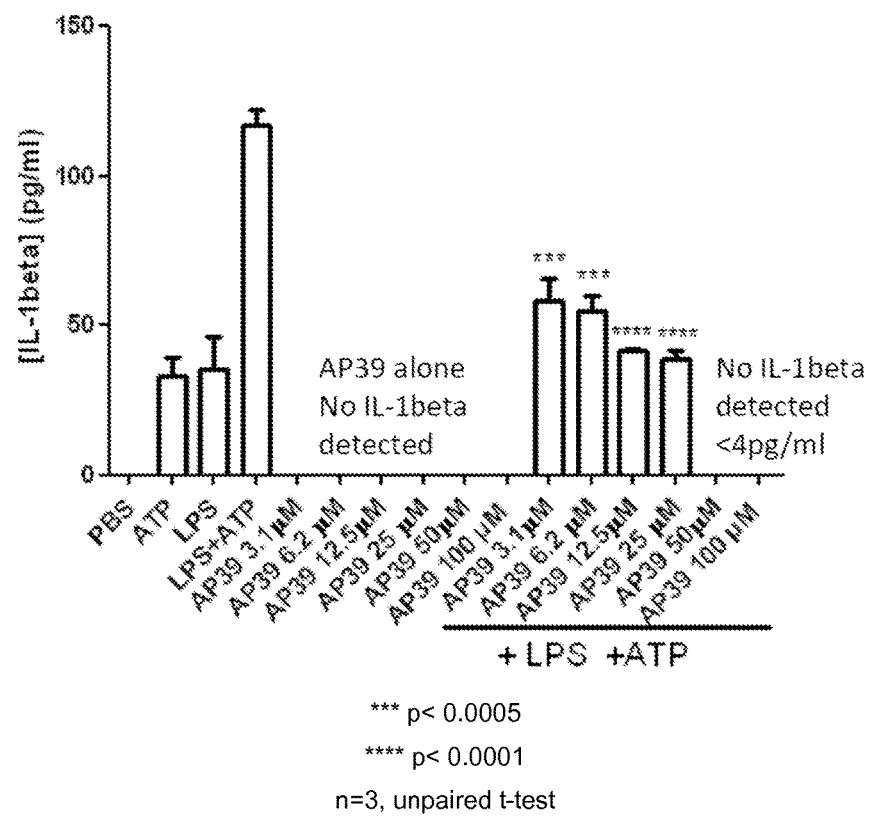
FIG. 35 is a graph showing the effects of AP39 on the activation of the inflammasome in human THP-1 cells.
Figure 36:
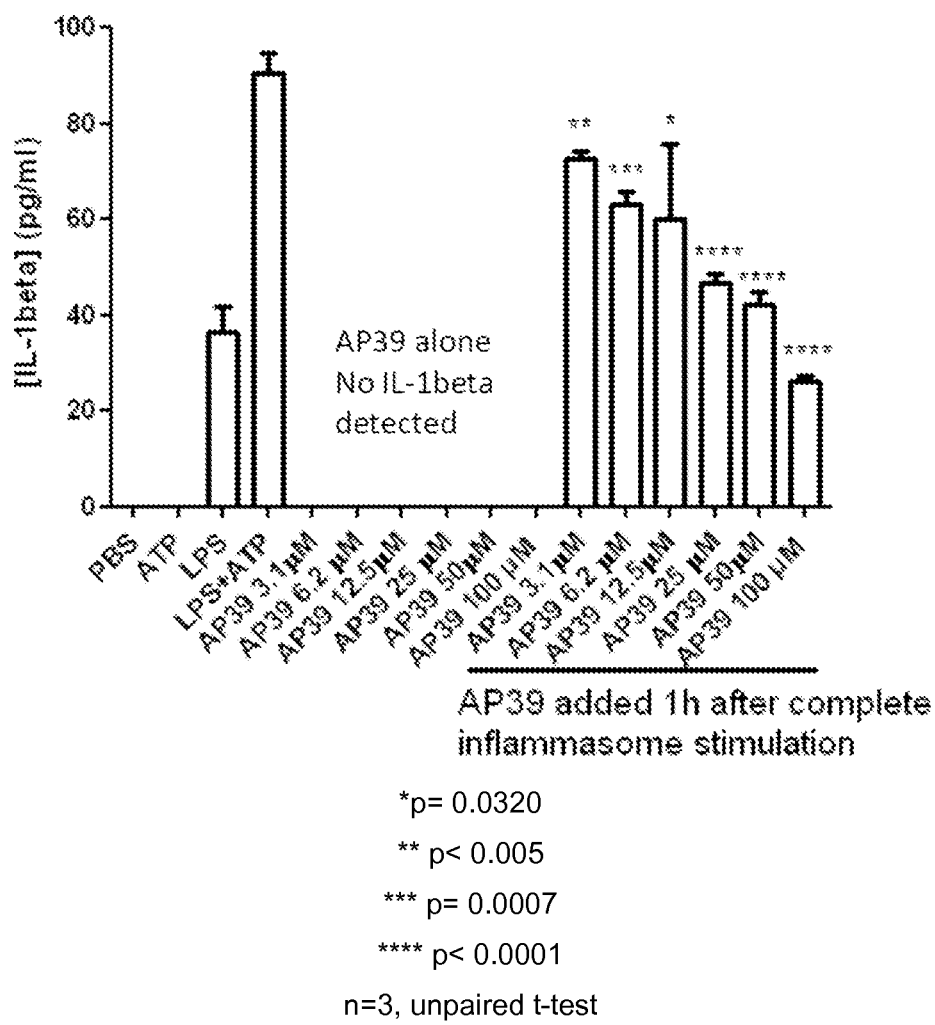
FIG. 36 is a graph showing the effects of AP39 on inflammasome activity after activation by LPS and ATP in human THP-1 cells.

In both experiments, after these time periods the levels of native mitochondrial matrix protein peroxiredoxin 3 (Prx3) (dimer, molecular weight 37 kDa) and over-oxidised Prx3 (monomer, molecular weight 25 kDa) were determined by standard western blotting procedures (M Whiteman et al (FASEB J, 2004, 18, 1395-1397) (FIGS. 32 and 33).
Determination of Nrf2 Activation Nrf2 activation was studied in AREc32 cells. This stable cell line is derived from MCF-7 cells transfected with a construct containing eight copies of the rat glutathione-S-transferase-A2 Antioxidant Response 211 Element (ARE) and the SV40 promoter sequence upstream of a firefly luciferase reporter gene (Wang, X. J. et al., 2006, Cancer Res, 66, 10983-94). The cells were pre-treated for 4 h with the non-mitochondria targeted slow release $H_2S$ donor GYY4137 (6.25 µM) and the mitochondria-targeted $H_2S$ donor AP39 (6.25 µM). After 4 h the treatments were removed and the cells were treated with sulforaphane (12.5 µM), an Nrf2-activator and positive control, for 24 hrs. Nrf-2 activation (luciferase activity) was then assessed by luminescence with a BMG labtech Omega microplate reader (FIG. 34). Data are expressed as fold induction of luciferase activity normalised to cell biomass (sulforhodamine B).
Determination of Inhibition of Inflammasome Activation Human THP-1 cells were cultured in RPMI medium and incubated with AP39 and bacterial endotoxin (lipopolysaccharide; LPS) (1 µg/ml) for 24 hrs, followed by ATP (5 mM) for an additional 24 hrs. After this time cell culture media was collected and inflammasome activation determined by measuring IL-10 levels in the culture media by commercial ELISA (Human IL-1 beta ELISA Ready-SET-Go, eBioscience) (FIG. 35). Data are mean+/−standard deviation (n=3).
Determination of Inhibition of Inflammasome Activity Once Inflammasone is Activated Human THP-1 cells were cultured in RPMI medium and exposed to bacterial endotoxin (lipopolysaccharide; LPS) (1 µg/ml) for 24 hrs, followed by ATP (5 mM) and AP39 for 24 hrs. After this time cell culture media was collected and inflammasome activity determined by measuring IL-1β levels in the culture media by commercial ELISA (Human IL-1 beta ELISA Ready-SET-Go, eBioscience) (FIG. 36). Data are mean+/−standard deviation (n=3).
Discussion of the Results The results in the Figures show that AP39 and GYY4137 inhibit cell death, mitochondrial dysfunction, mitochondrial and cytoplasmic oxidative stress when cells are challenged with a range of physiological oxidant species. AP39 was substantially more potent at mediating these effects than a non-mitochondria targeted $H_2S$ donor (GYY4137) e.g. 50-200 nM AP39 cf. 100-500 μM GYY4137.

FIG. 1 shows the amount of $H_2S$ generated from AP39 and AP123 after 1 hr incubation at room temperature in phosphate buffer, pH 7.4.

Figure 2:
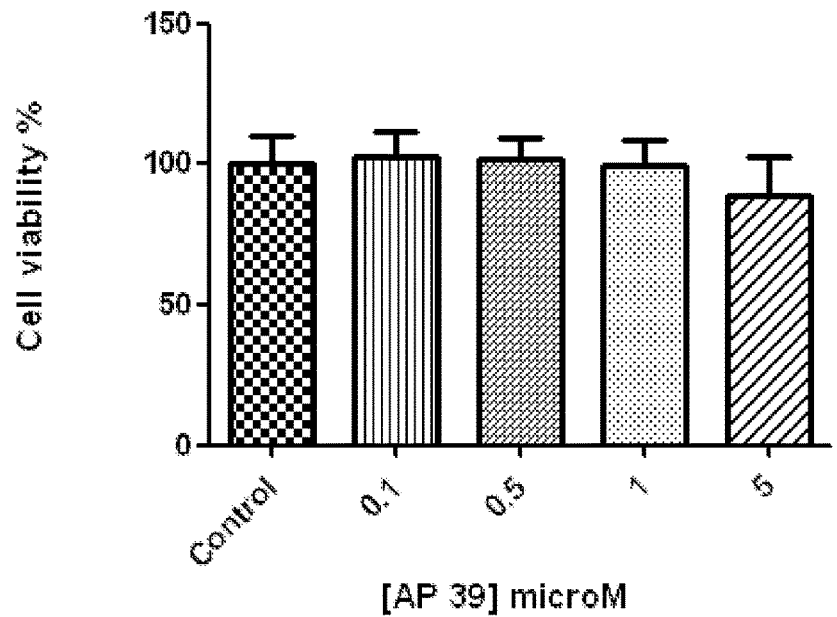
FIG. 2 is a histogram that shows the % cell viability of human brain microvascular endothelial cells (HMEC) that have been incubated with AP39.
Figure 3:
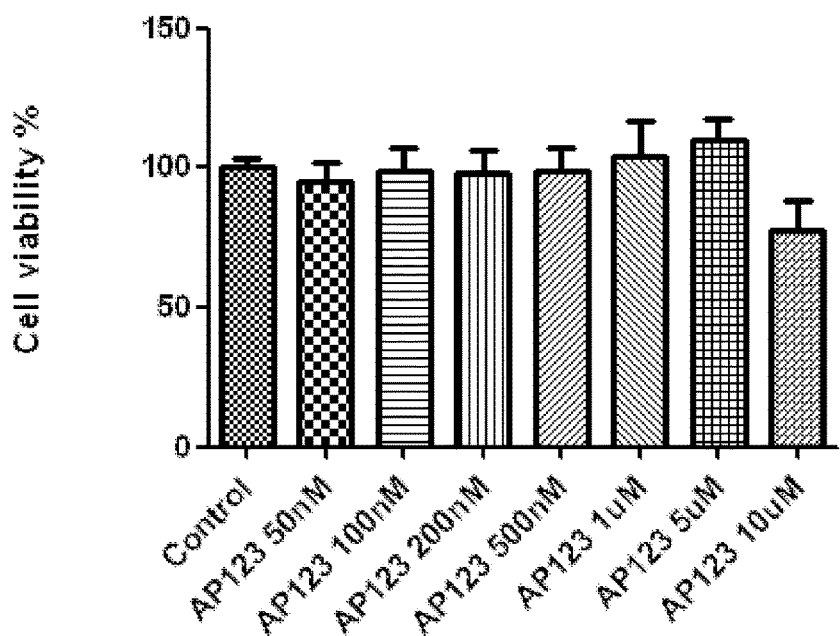
FIG. 3 is a histogram that shows the % cell viability of HMEC that have been incubated with AP123.

FIGS. 2 and 3 show that incubation of HMEC with up to 5 μM of AP39 or up to 10 μM of AP123 did not induce significant cytotoxicity in HMEC (i.e. under the experimental conditions employed in the subsequent assays, AP39 and AP123 were not toxic).

Figure 4:
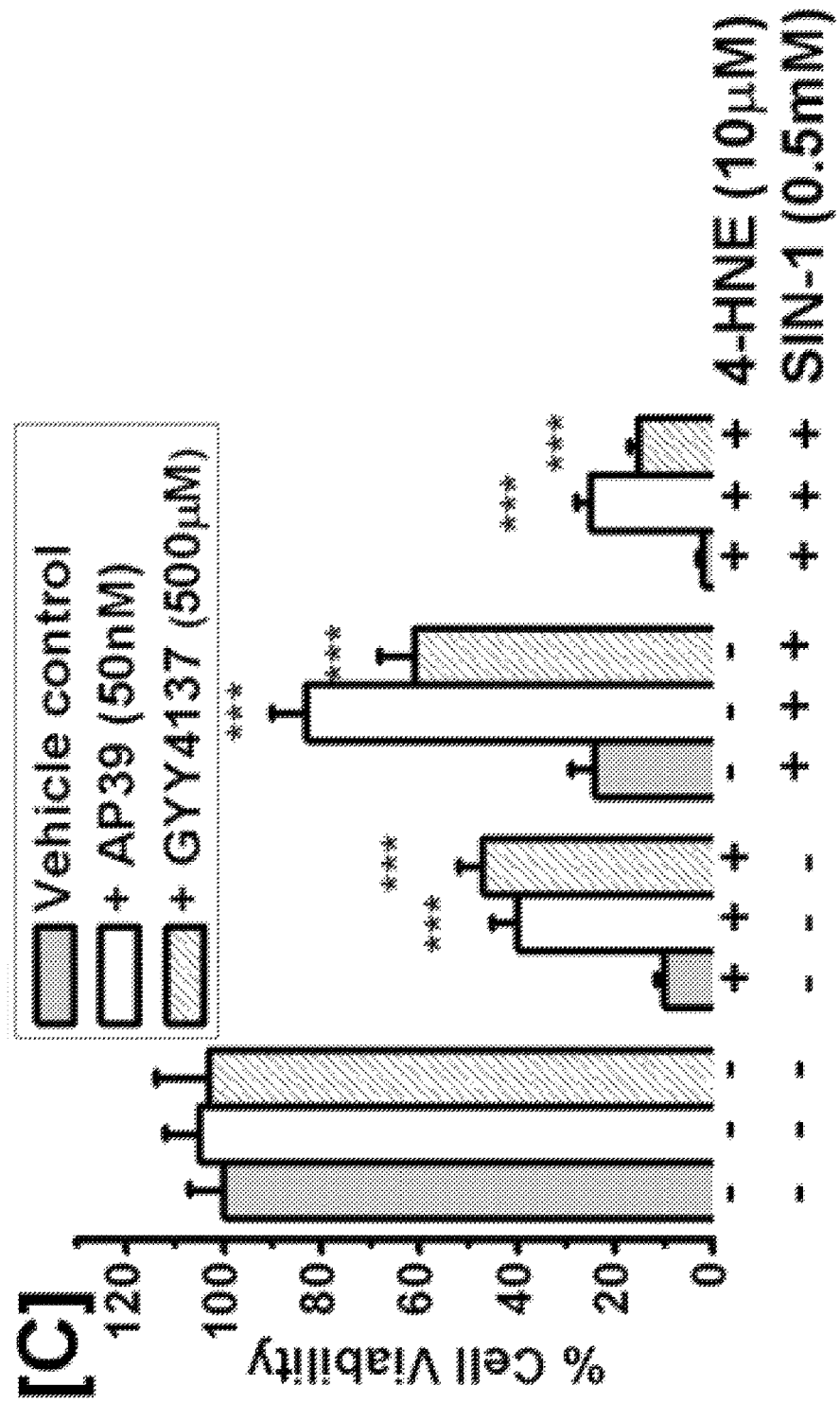
FIG. 4 is a comparison of cytoprotection by mitochondria-targeted and non-targeted $H_2S$ donors on cell death induced by 4-hydroxynonenal (4-HNE) and 3-morpholino-sydnonimine hydrochloride (SIN-1) toxicity in HCMEC/D3 cells. GYY4137 is a non-targeted $H_2S$ donor compound, morpholin-4-ium 4-methoxyphenyl(morpholino) phosphinodithioate.

The results shown in FIG. 4 permit direct comparison of the effects of GYY4137 (500 μM, used as a non-mitochondria targeted $H_2S$ donor for control purposes) with AP39 (added at a final concentration of 50 nM) against cell death induced by the oxidants SIN-1 and 4-HNE alone, and SIN-1 and 4-HNE in combination. Both AP39 and GYY4137 significantly inhibited SIN-1 and 4-HNE induced cell death. AP39 was effective when added at a final concentration of 50 nM, whereas similar cytoprotection was observed with GYY4137 at 500 μM. The data are shown as the mean+/−standard deviation of 6 or more separate determinations (***=$p<0.001$ compared to oxidant treated cells).

The data in FIG. 4 suggests that mitochondrial targeting of $H_2S$ confers greater cytoprotection than non-targeted donor molecules.

Figure 5:
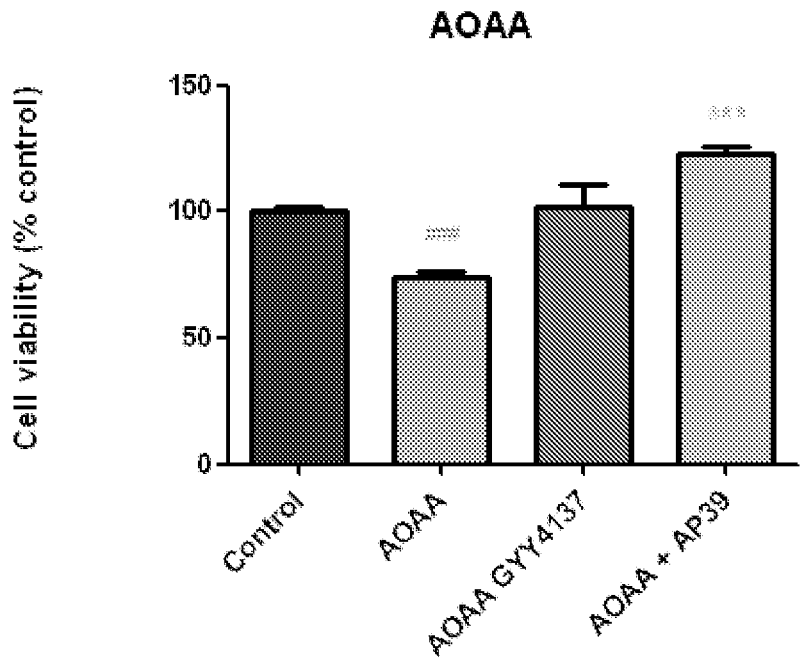
FIG. 5 is a histogram that shows the effect of aminooxyacetate (AOAA), which is a cystathionine-β-synthase (CBS) inhibitor, on endogenous $H_2S$ production alone and in combination with the $H_2S$ releasing compounds GYY4137 and AP39.
Figure 6:
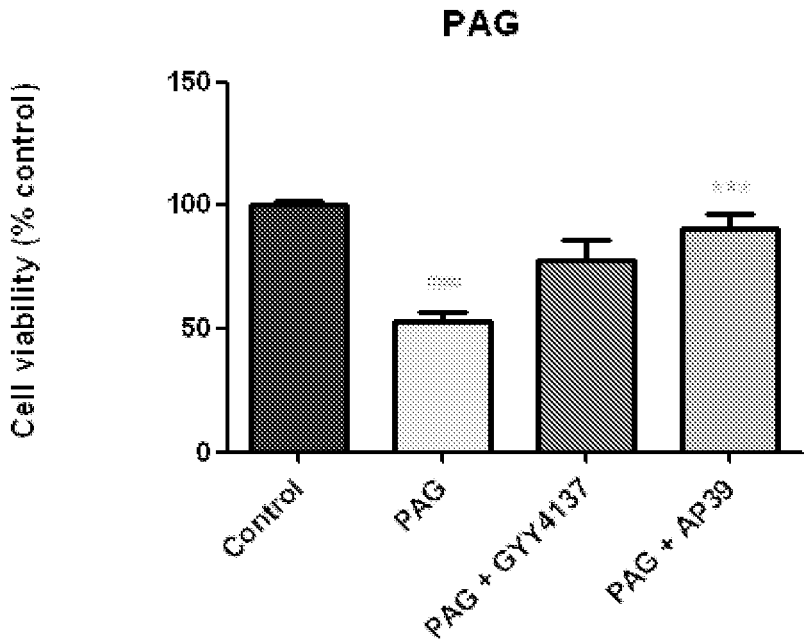
FIG. 6 is a histogram that shows the effect of propargylglycine (PAG), which is a cystathionine-γ-lyase (CSE) inhibitor, on endogenous $H_2S$ production alone and in combination with the $H_2S$ releasing compounds GYY4137 and AP39.
Figure 7:
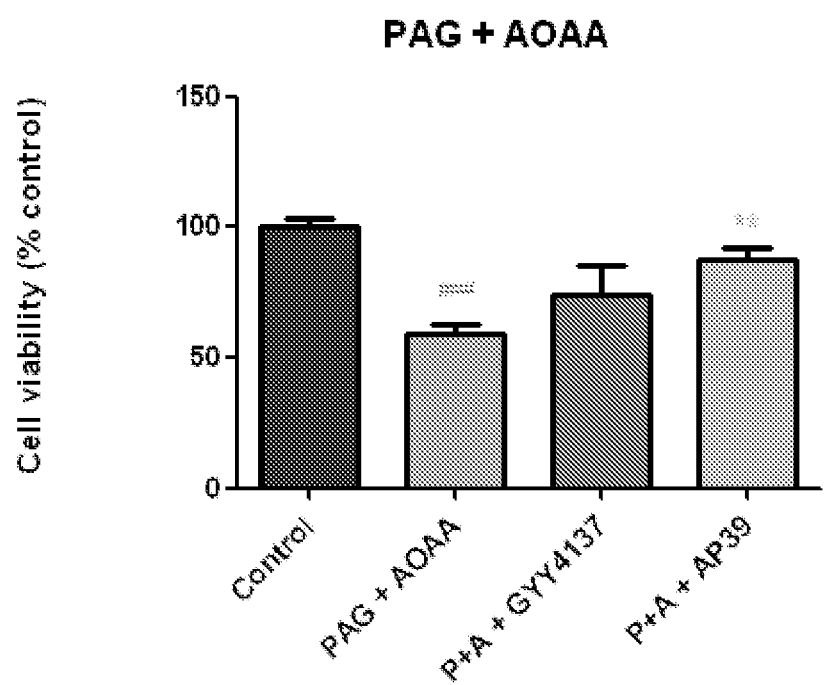
FIG. 7 is a histogram that shows the effect of PAG and AOAA on endogenous $H_2S$ production in combination with the $H_2S$ releasing compounds GYY4137 and AP39.

FIGS. 5 to 7 show that incubation of HMEC with the CBS inhibitor AOAA (FIG. 5), the CSE inhibitor PAG (FIG. 6) or a combination of AOAA with PAG (FIG. 7) to inhibit endogenous $H_2S$ synthesis, significantly decreased cellular viability suggesting endogenous $H_2S$ was required for cell survival. In the data shown in FIGS. 5 to 7, ###=$p<0.001$ compared to the control; ***=$p<0.001$ compared to inhibitors. Incubation of HMEC with GYY4137 (100 μM) or AP39 (100 nM) significantly inhibited AOAA (FIG. 5), PAG (FIG. 6) and AOAA/PAG (FIG. 7), induced cell death as well suggesting replacement of cellular $H_2S$ generation with $H_2S$ donors was cytoprotective.

Figure 8:
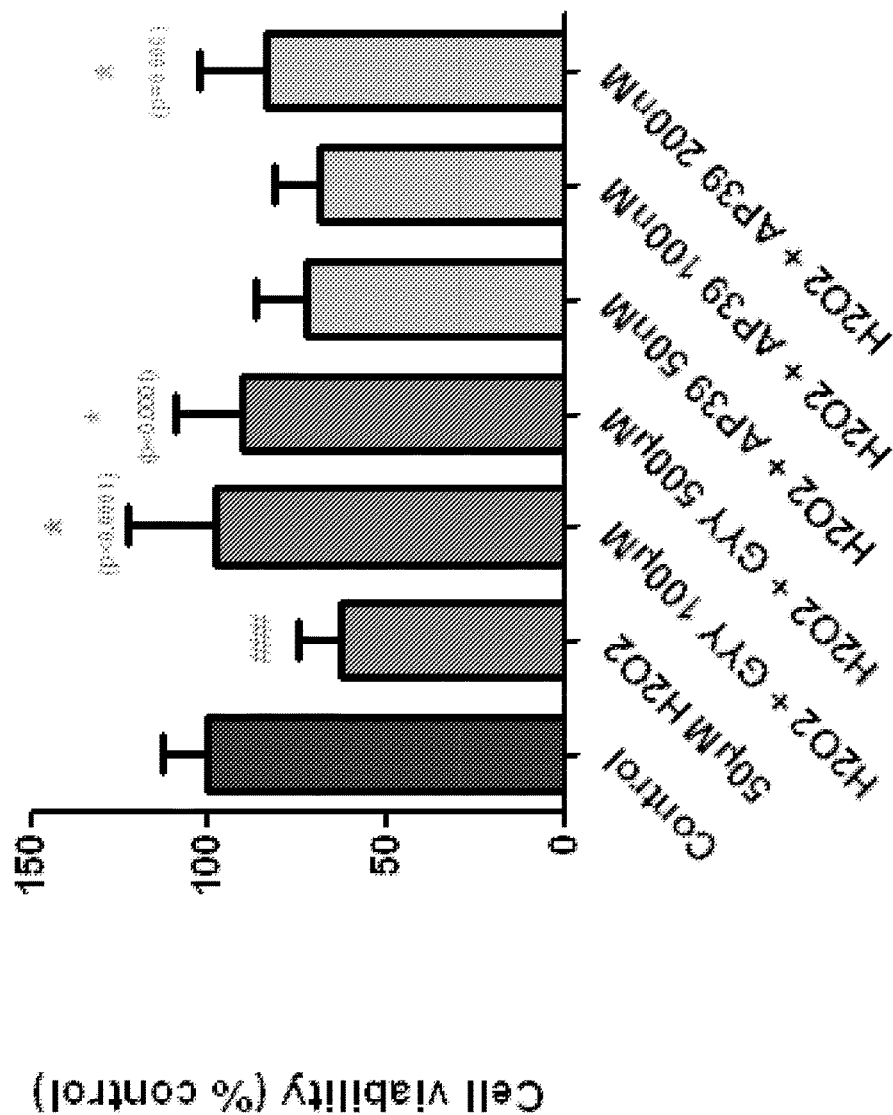
FIG. 8 is a histogram showing the protective effect of GYY4137 and AP39 against oxidative stress induced by $H_2O_2$ (50 to 200 μM).

FIG. 8 shows that incubation of HMEC with 50 μM of the oxidant $H_2O_2$ induced significant cytotoxicity. $H_2O_2$-induced cytotoxicity was inhibited by treatment of cells with either the non-targeted $H_2S$ donor GYY4137 (100-500 μM) or the mitochondrial targeted $H_2S$ donor AP39 (50-200 nM).

Figure 9:
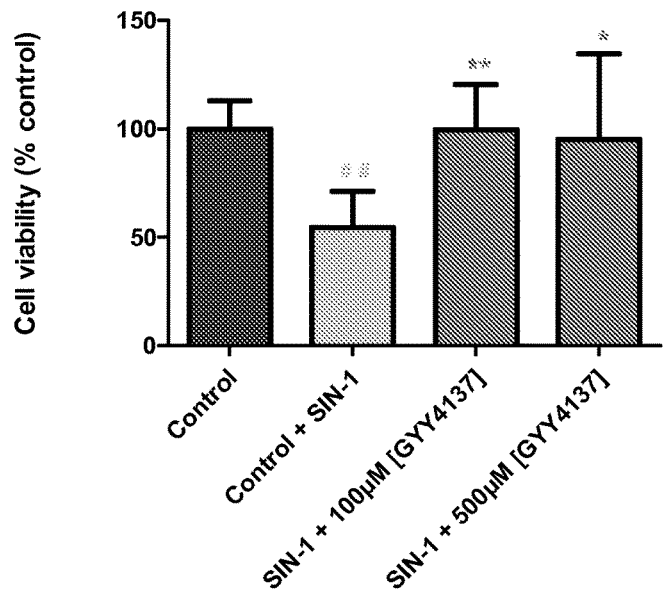
FIG. 9 is a histogram showing the protective effect of GYY4137 against oxidative stress induced by SIN-1 (500 μM).
Figure 10:
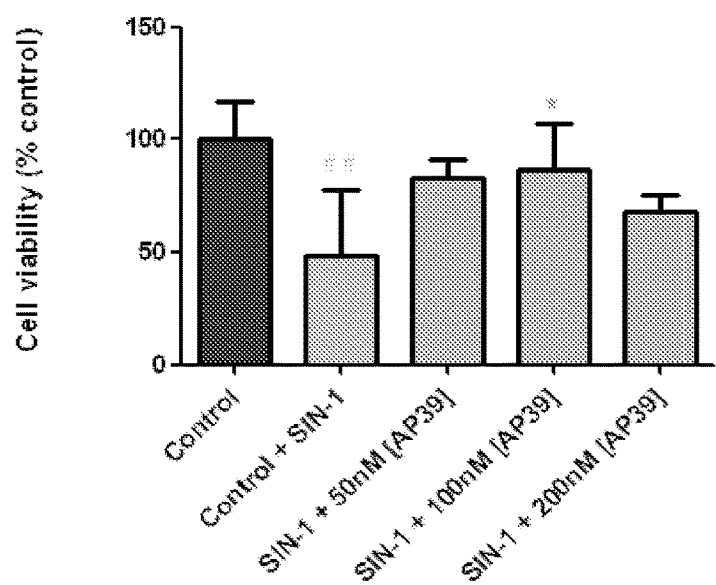
FIG. 10 is a histogram showing the protective effect of AP39 against oxidative stress induced by SIN-1 (500 μM).

FIGS. 9 and 10 show that GYY4137 (100 μM and 500 μM; FIG. 9) and AP39 (50-200 nM; FIG. 10) significantly inhibited cell death induced by SIN-1 (500 μM).

Figure 11:
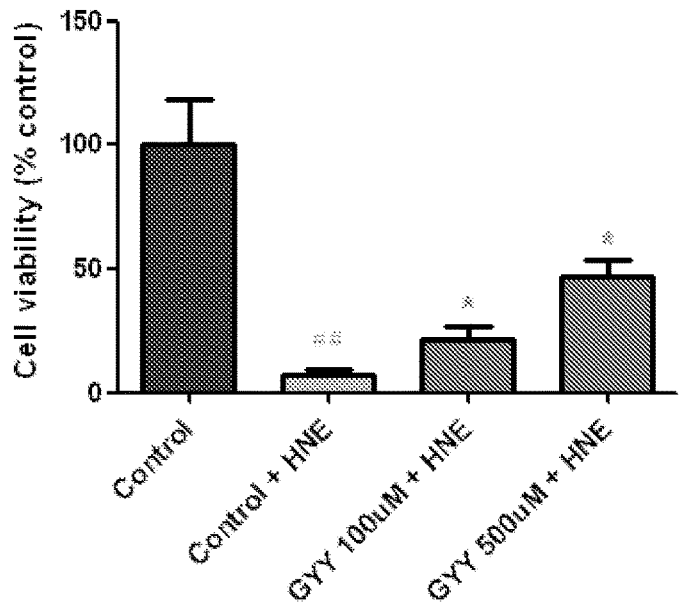
FIG. 11 is a histogram showing the protective effect of GYY4137 against oxidative stress induced by 4-HNE (10 μM).
Figure 12:
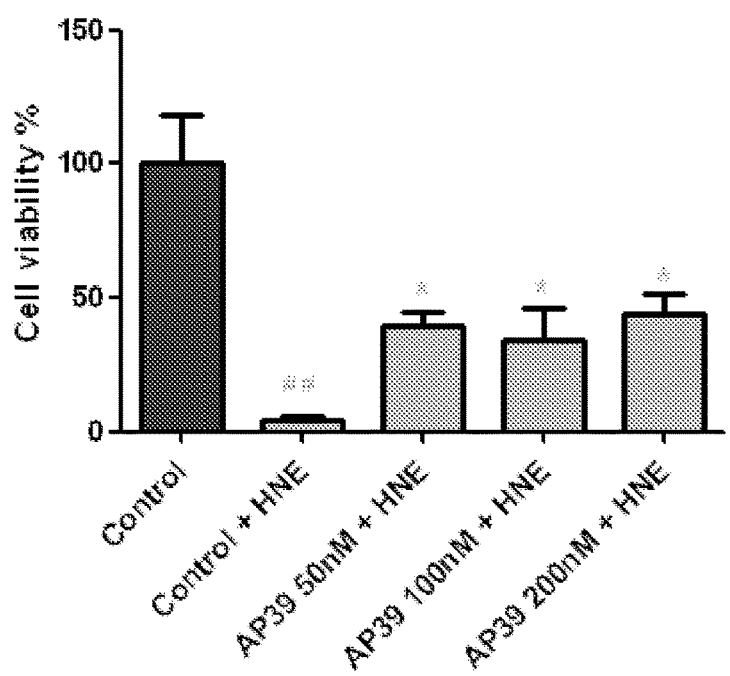
FIG. 12 is a histogram showing the protective effect of AP39 against oxidative stress induced by 4-HNE (10 μM).

FIGS. 11 and 12 show that GYY4137 (100 μM and 500 μM; FIG. 11) and AP39 (50-200 nM; FIG. 12) significantly inhibited cell death induced by 4-HNE (10 μM).

Figure 13:
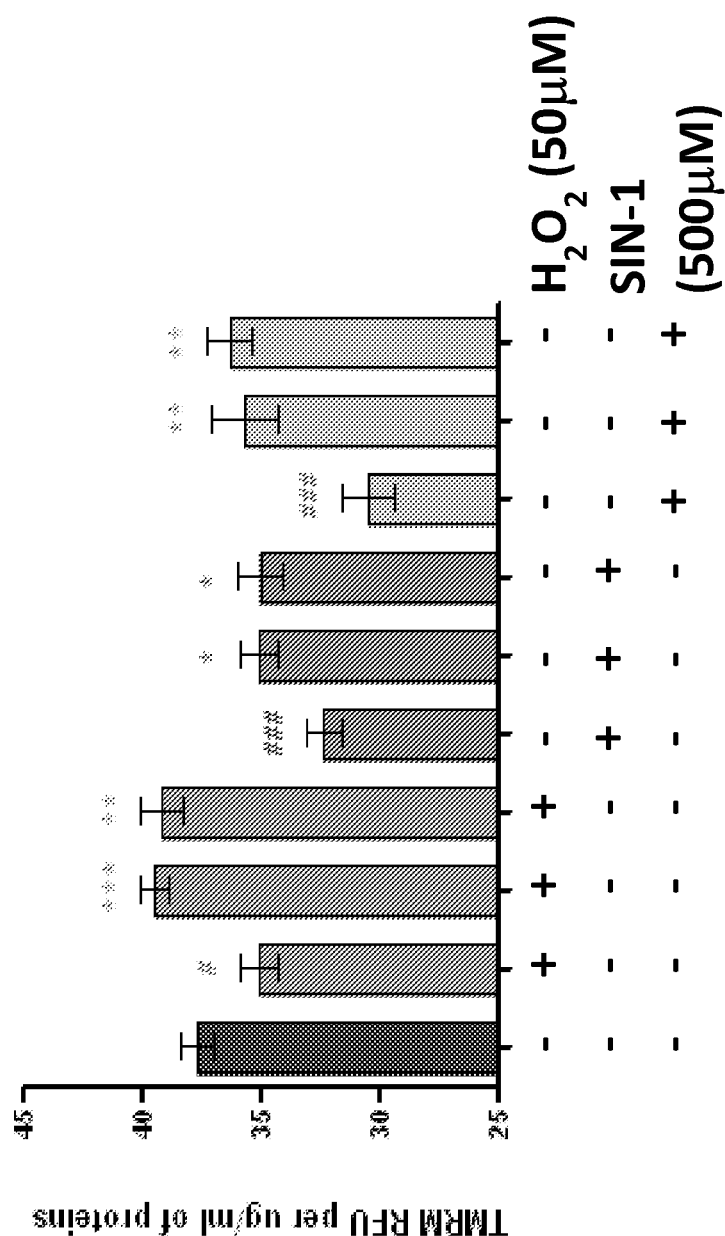
FIG. 13 is a histogram showing the mitochondrial membrane potential (ΔΨm) of human cerebral microvascular endothelial cells (HCMEc) in the presence of oxidative stress agents ($H_2O_2$, SIN-1 or 4-FINE) and the $H_2S$ releasing compounds GYY4137 and AP39.

FIG. 13 shows the inhibition of oxidant-induced mitochondrial membrane potential (Δψm) collapse by GYY4137 (100 μM) and AP39 (100 nM) and suggests mitochondrial delivery of $H_2S$ by AP39 confers significantly greater cytorprotection than a non-targeted $H_2S$ donor molecule. In FIG. 13, #=$p<0.001$ compared to the control; *=$p<0.001$ compared to the oxidative stress agent.

Figure 14:
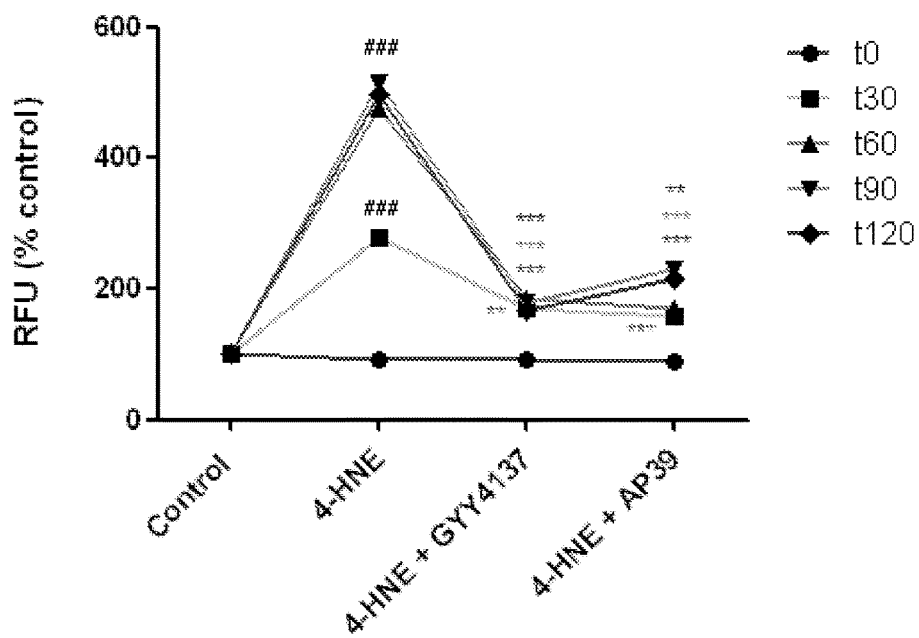
FIG. 14 is a graph showing cytoplasmic oxidative stress induced by 4-HNE by a dichlorofluorescein assay (DCFDA assay). GYY4137 (100 μM) and AP39 (100 nM) significantly decreased 4-HNE mediated increase in intracellular oxidant species.
Figure 15:
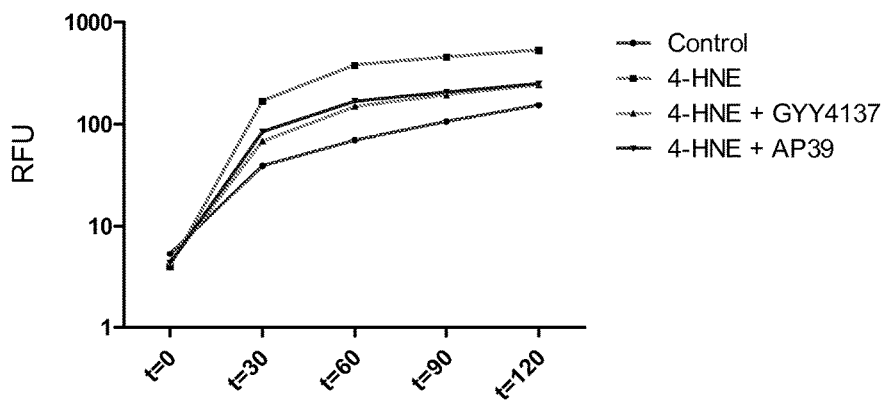
FIG. 15 is a graph showing that the time dependent increase in intracellular oxidative stress (DCFDA assay) was reduced by pretreatment of cells with either GYY4137 (100 μM) or AP39 (100 nM).

FIGS. 14 and 15 show that the generation of cytoplasmic oxidant species by 4-FINE. Both GYY4137 (100 μM) and AP39 (100 nM) significantly reduced the formation of 4-HNE-derived intracellular oxidants suggesting $H_2S$ release by these compounds could interact with detrimental oxidant species to prevent cell death.

Figure 16:
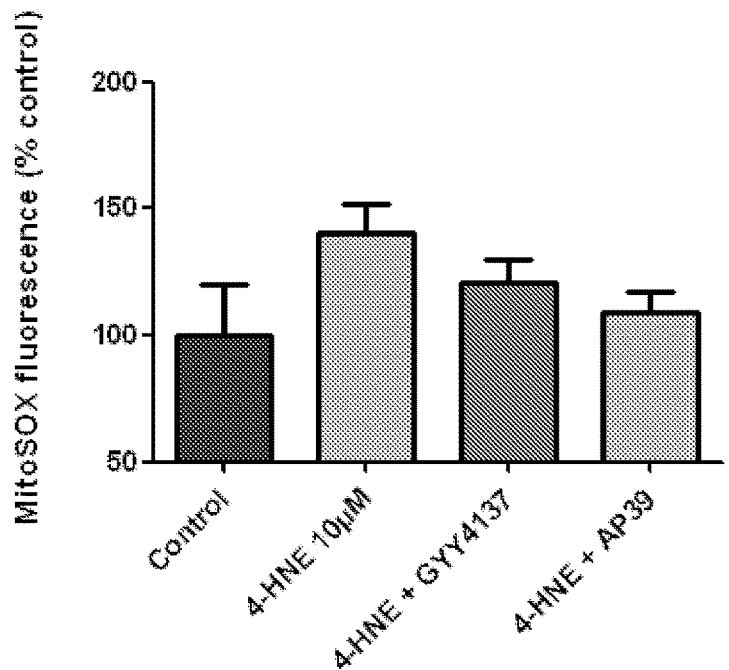
FIG. 16 is a histogram showing the mitochondrial oxidative stress as determined by the MitoSOX red assay (a mitochondria-specific superoxide indicator).

FIG. 16 shows that 4-HNE induced mitochondrial production of superoxide, a detrimental oxidant species. Both GYY4137 and AP39 reduced mitochondrial superoxide formation suggesting the reduction of mitochondrial-derived intracellular oxidant stress by $H_2S$ could be a mechanism for GYY4137 and AP39-mediated cytoprotection. 4-HNE was used in a concentration of 10 μM, GYY4137 was used in a concentration of 100 μM and AP39 was used in a concentration of 0.1 μM. Since AP39 did this at 1,000 fold lower concentration it would also suggest that AP39 targeting the mitochondria (with AP39 derived $H_2S$) was responsible in this disparity between concentrations used.

Figure 17:
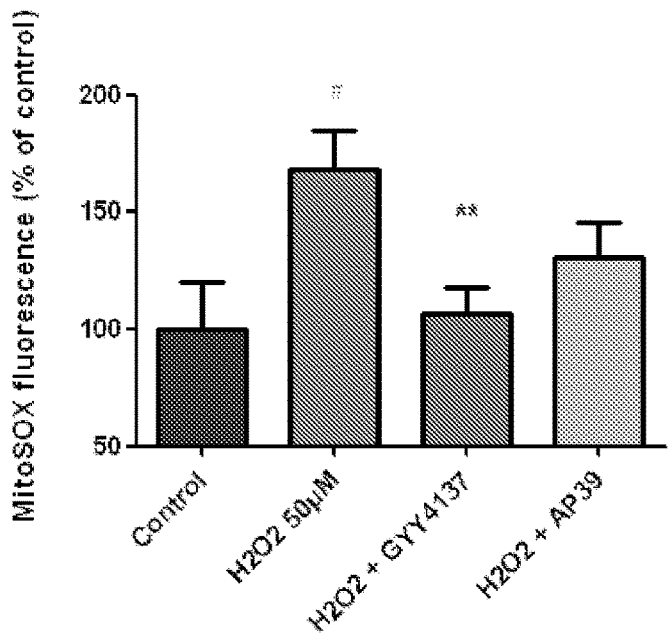
FIG. 17 is a histogram showing the mitochondrial oxidative stress as determined by the MitoSOX red assay (a mitochondria-specific superoxide indicator). GYY4137 and AP39 reduced mitochondrial superoxide formation induced by $H_2O_2$.
Figure 18:
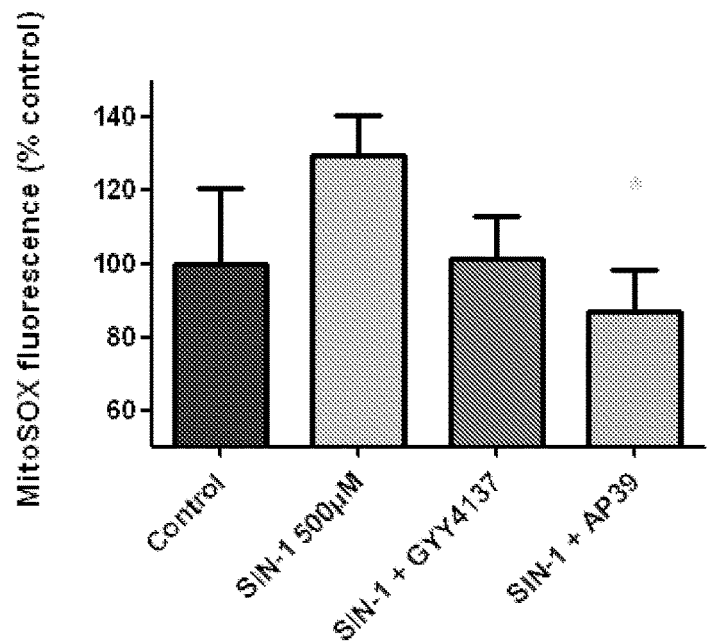
FIG. 18 is a histogram showing the mitochondrial oxidative stress as determined by the MitoSOX red assay (a mitochondria-specific superoxide indicator).

FIG. 17 shows that both $H_2S$ donors were not as effective at reducing intracellular oxidative stress (cytoplasmic, using the DCFDA assay) when cells were treated with the non-specific oxidant $H_2O_2$. In contrast, AP39 (100 nM) significantly reduced mitochondria-derived oxidant production (MitoSox Red assay) induced by 4-HNE (FIG. 18), a cytotoxic lipid peroxide well known to induce mitochondrial stress and cell death. $H_2O_2$ was used in a concentration of 50 μM, SIN-1 was used in a concentration of 500 μM, GYY4137 was used in a concentration of 100 μM and AP39 was used in a concentration of 0.1 μM.

Figure 19:
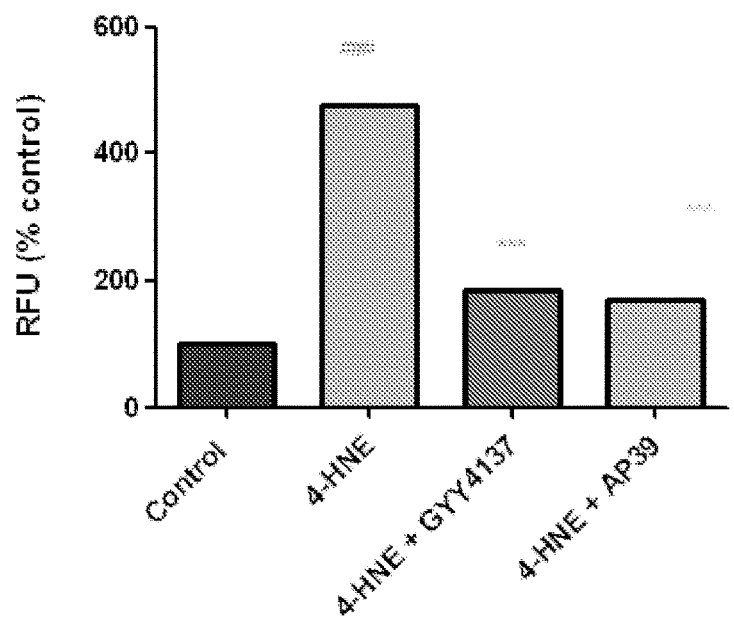
FIG. 19 is a histogram showing the effect that GYY4137 (100 μM) or AP39 (100 nM) have in inhibiting intracellular oxidative stress in the presence of the oxidative stress agent 4-FINE.

FIG. 19 shows the effect that GYY4137 (100 μM) or AP39 (100 nM) have in inhibiting intracellular oxidative stress in the presence of the oxidative stress agent 4-HNE.

FIG. 20 shows the contrasting effects of injecting 1.6 μM/kg and 2.7 μM/kg AP39 or 3 μM/kg $Na_2S$ into anaesthetised Wistar (normotensive) rats. AP39 reduced (a) blood pressure and (b) heart rate and transiently increased breathing rate. In contrast, there was no effect of $Na_2S$ on either of these parameters, highlighting the differences between a mitochondria targeted slow release $H_2S$ donor molecule and the bolus addition of $Na_2S$, a 'fast-releasing' and non-mitochondria targeted $H_2S$ generating compound.

FIG. 21 shows the effects on blood pressure (A), heart rate (B) and breathing rate (C) of injecting spontaneously hypertensive rats (SHR) with 1.5 μM/kg AP39. Sustained blood pressure lowering effects are seen (A).

FIG. 22 shows the effects of (A) blood pressure and (B) heart rate in anaesthetised Wistar rats of a higher concentration of AP39 (4 μM/kg) and shows sustained blood pressure (A) and heart rate (B) lowering effects. This was not observed with the 'fast-release' and non-mitochondria targeted compound $H_2S$ donor compound $Na_2S$ (FIG. 20).

FIGS. 20 to 22 show that AP39 is about 10-50 times more effective than $Na_2S$ at influencing the blood pressure, heart rate and breathing rate of rats.

FIG. 23 shows the vasodilatory effects of increasing concentrations of AP39 (1-5 μM) on adrenaline-precontracted rat aorta (A-C) and mesenteric arteries (D).

Figure 24:
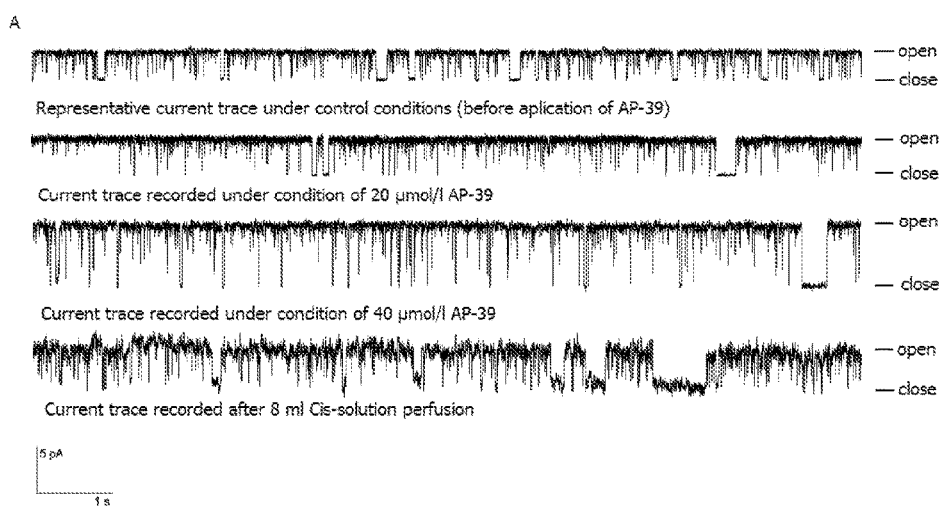
FIG. 24 is a graph which shows the effects of AP39 (20 and 40 μM) on the amplitude of the electrical current through the single chloride channels derived from rat heart sarcoplasmic reticulum at 0 mV.
Figure 25:
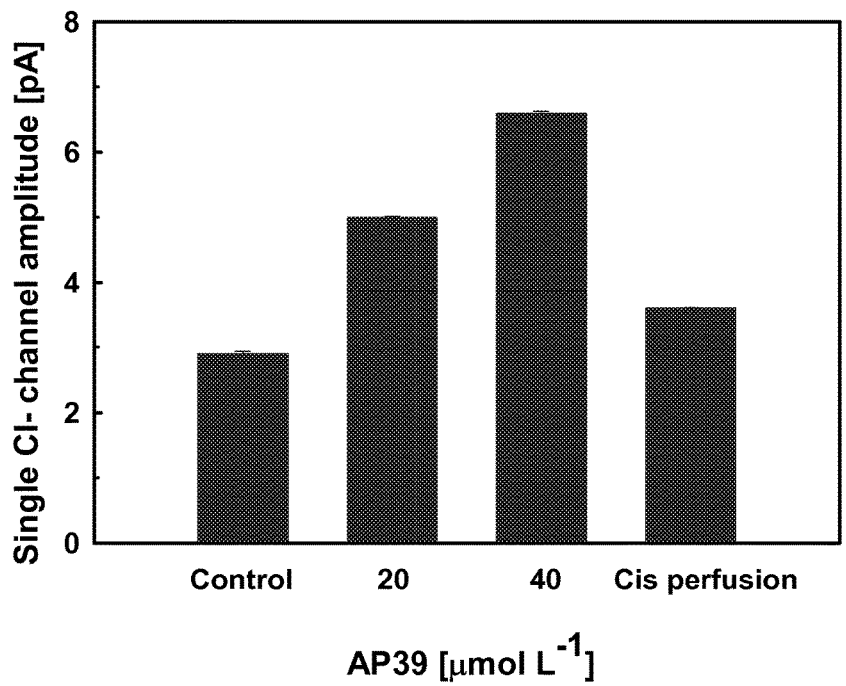
FIG. 25 is a histogram which shows the effects of AP39 (20 and 40 μM) on the amplitude of the electrical current through the single chloride channels derived from rat heart sarcoplasmic reticulum at 0 mV.

FIGS. 24 and 25 show the effects of AP39 on the amplitude of the electrical current through the single chloride channels derived from rat heart sarcoplasmic reticulum at 0 mV; AP39 increased the amplitude of chloride currents through the channel.

Figure 26:
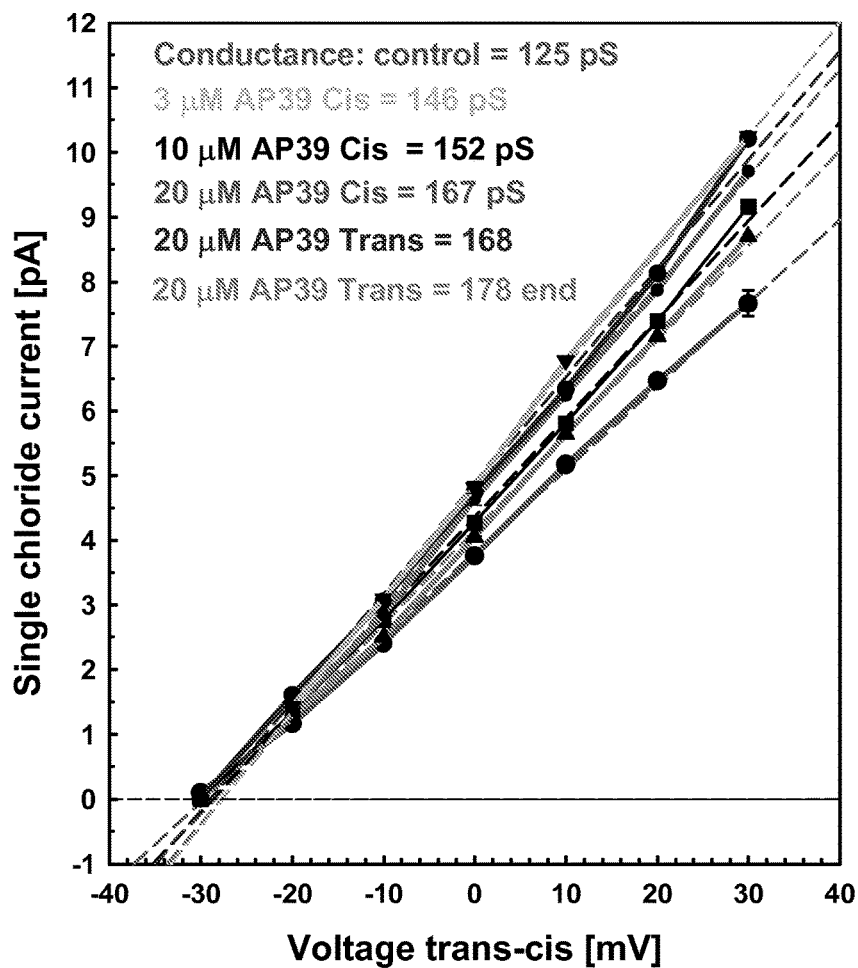
FIG. 26 is a graph which shows the effects of AP39 on conductance of chloride channels derived from sarcoplasmic reticulum of rat heart. Conductance of the control channel was 125 pS.
Figure 27:
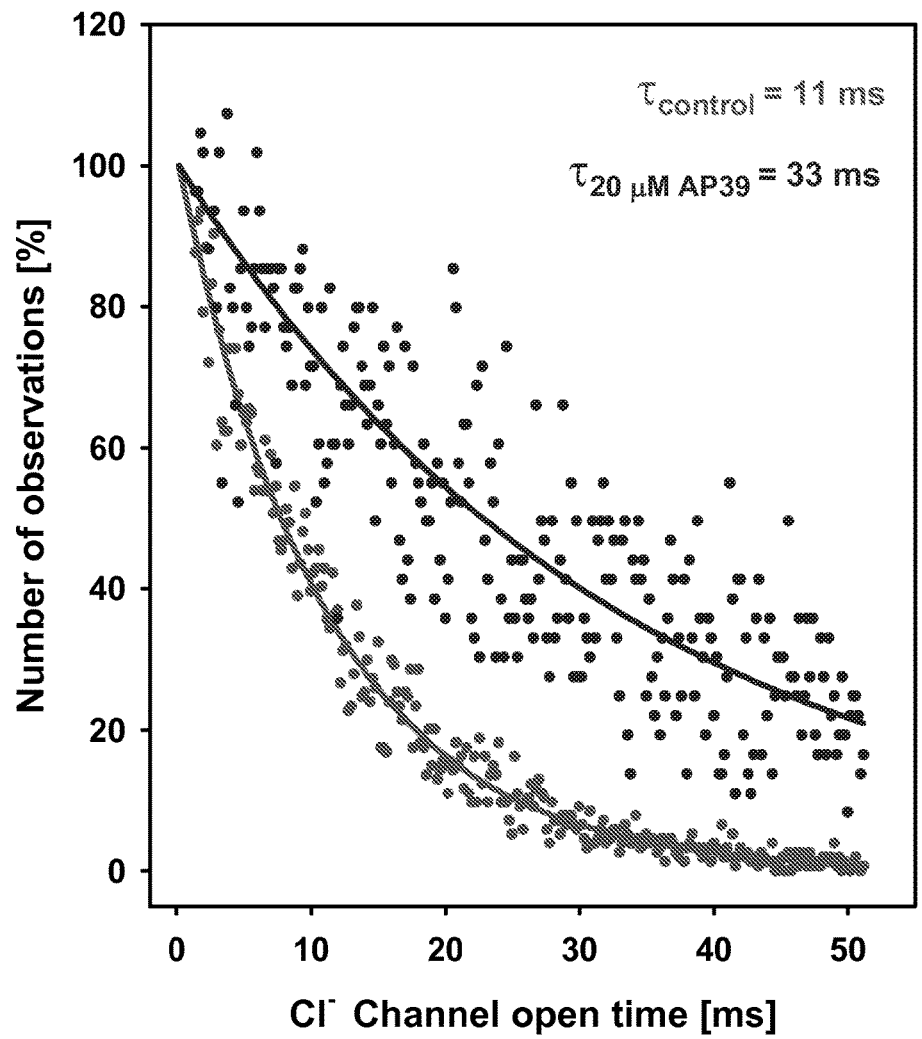
FIG. 27 is a graph which shows the effects of AP39 (20 μmol/%) on the number of channel openings versus dwell time of the open channel.

FIG. 26 shows that AP39 increased conductance of the CL channels. The reversal potential of control channel was ∼−31 mV, which indicates a $Cl^-/K^+$ permeability ratio of 9.6. AP39 did not influence channel reversal potential (∼−31 mV), i.e. it did not influence $Cl^-/K^+$ channel permeability ratio in isolated rat heart sarcoplasmic reticulum. FIG. 27 shows that the mean open time of the channel was 11 ms at 0 mV. AP39 (20 μmol/l) increased the mean open time to 33 ms demonstrating that AP39 had a tendency to stabilize the open stage of the chloride channel in rat heart sarcoplasmic reticulum.

Figure 28:
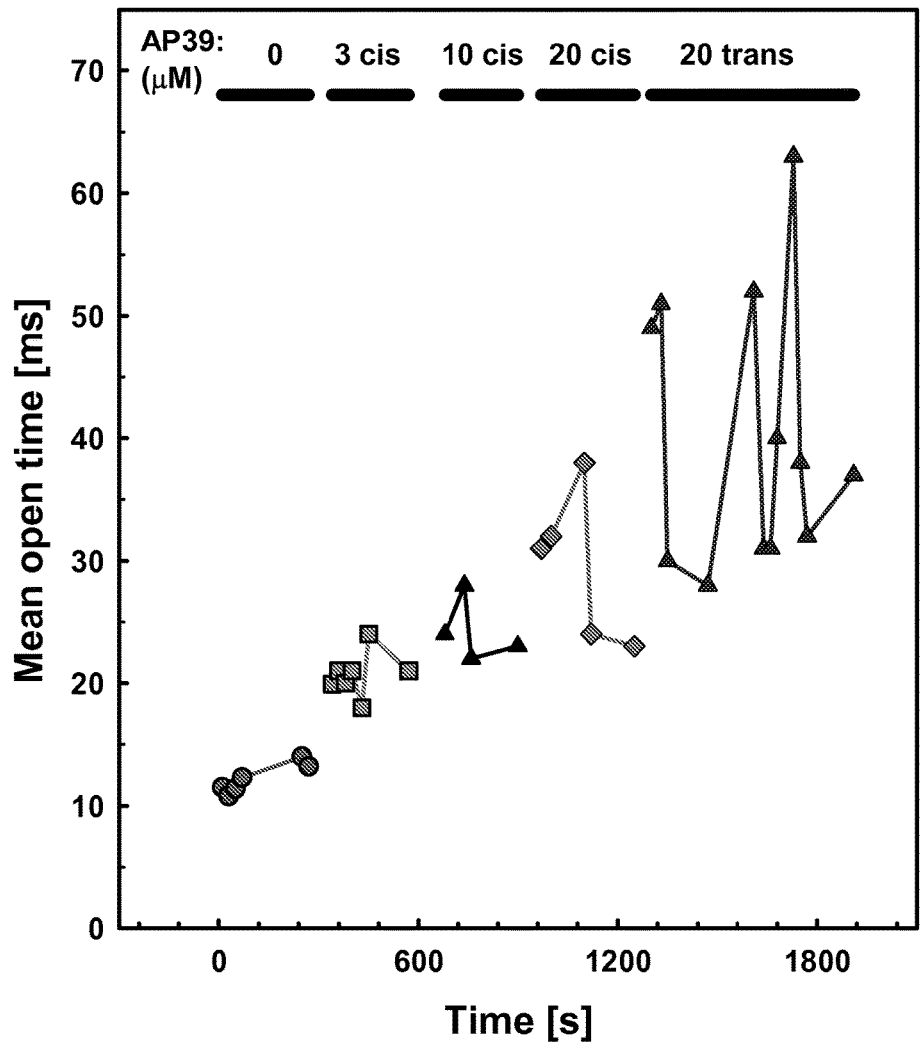
FIG. 28 is a graph which shows the effect of AP39 on the probability to be open of the chloride channel in the concentration dependent manner.

FIG. 28 shows that AP39 increased the mean chloride channel open time in a concentration dependent manner in rat heart sarcoplasmic reticulum.

FIGS. 24-28 show that AP39 interacts with chloride channels derived from the rat heart sarcoplasmic reticulum and modulates its single channel activities: AP39 activates the channel by increasing Cl– current amplitude and conductance; and AP39 increased the channel open probability by increasing channel mean open time.

FIG. 29-31 show that AP39 (>300 nM) inhibited CAv3.1 T-type calcium channels in human embryonic kidney (HEK293) cells in both a concentration (FIGS. 29 and 31) and a time-dependent (FIG. 30) manner.

The above data show that the mitochondria-targeted $H_2S$ donor molecule AP39 is vasoactive in vivo, reducing blood pressure and heart rates in normotensive (Wistar) and hypertensive (SHR) rats as well as vasodilatory ex vivo using isolated rat aortic and mestenteric arteries. In contrast, $Na_2S$, a non-mitochondrially targeted donor of $H_2S$ did not reduce blood pressure and did not decrease heart rate in Wistar or SHR rats. Part of the mechanism for these observations was by action on smooth muscle sarcoplasmic reticulum ion channels, specifically opening of chloride channels and inhibition of T-type calcium channels.

FIGS. 32 and 33 show western blotting analysis of a mitochondrial matrix located antioxidant enzyme, peroxiredoxin 3 (Prx3) in human THP-1 cells after exposure to oxidative stress inducing agent $H_2O_2$ and increasing concentrations of AP39. The western blotting assays show that AP39 reduced the levels of the over-oxidised monomeric form of the mitochondrial matrix protein Prx3; in the experiment resulting in FIG. 33 (where the human THP-1 cells were exposed to different concentrations of AP39 for 4 hours followed by the addition of $H_2O_2$ for 1 minute), Prx3 oxidation by $H_2O_2$ was reduced by 5 µM AP39. FIGS. 32 and 33 show that AP39 preserved the activity of enzyme Prx3, and that AP39 targeted the mitochondrial matrix, inducing effects within the mitochondrial matrix.

FIG. 34 shows the activation of the transcription factor Nrf2 in human AREc32 cells in the presence of sulforaphane (used as a positive control), a non-mitochondria targeted slow release $H_2S$ donor (GYY4137) and AP39. Nrf2 is a key transcription factor regulating among other things cellular defence mechanisms against oxidative stress. The figure highlights that AP39 activates the transcription factor Nrf2, and that at equimolar concentrations, AP39 was more potent that GYY4137 at inducing Nrf2 transcription factor activation.

FIG. 35 shows the effects of AP39 on inflammasome activation induced by LPS/ATP in THP-1 cells. AP39 reduced IL-1β levels in the cell culture media, indicating that AP39 inhibited the activation of the inflammasome.

FIG. 36 shows the effects of AP39 on inflammasome activity in THP-1 cells. The inflammasome was activated using LPS/ATP, and the ability of AP39 to subsequently reduce IL-1β levels, indicative of inhibiting inflammasome activity, was determined by ELISA. The figure shows that AP39 inhibited inflammasome activity after inflammasome activation by LPS/ATP.

FIGS. 35 and 36 therefore show that AP39 could prevent inflammasome activation (FIG. 35) as well as inhibit inflammasome activity (FIG. 36); both are consistent with an anti-inflammatory action of AP39. FIG. 36 also highlights the therapeutic potential of AP39 in reducing pro-inflammatory signalling once the inflammasome is activated.

The invention claimed is:
1. A compound represented by formula:

MTG-L-S wherein:
S is a group capable of releasing hydrogen sulfide selected from:

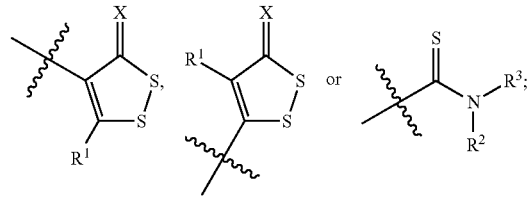

X represents S, O or N—OH;
$R^1$, $R^2$ and $R^3$ each independently represent hydrogen, $C_{1-12}$ alkyl, $C_{1-12}$ alkoxy or $C_{6-10}$ aryl, wherein each $C_{1-12}$ alkyl, $C_{1-12}$ alkoxy or $C_{6-10}$ aryl group is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl or halo-$C_{1-12}$-alkoxy substituents;
L is a linker represented by formula:

wherein:
L' is a straight chain alkylene group represented by formula

—$(CH_2)_n$— wherein n is an integer from 2 to 19;
Y represents —OC(O)— or —C(O)O—;
Z represents a phenylene group, which is unsubstituted or substituted by one, two, three or four substituents selected from a halogen atom, hydroxy, $C_{1-12}$ alkyl or a $C_{1-12}$ alkoxy group;
and
MTG represents a mitochondrial targeting group wherein the mitochondrial targeting group is a mitochondrial targeting peptide, or the mitochondrial targeting group is a lipophilic cation selected from a phosphonium cation, an arsonium cation, an ammonium cation, flupritine, MKT-077, a pyridinium ceramide, a quinolium, a liposomal cation, a sorbitol guanidine, a cyclic guanidine, or a rhodamine;
or a pharmaceutically acceptable salt of said compound.
2. The compound of claim 1, wherein the moiety —Y—Z— is represented by formula:

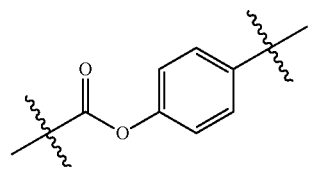

3. The compound of claim 1, wherein S is selected from

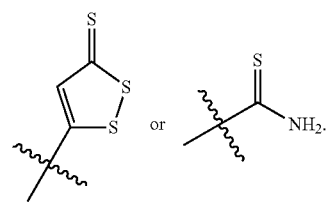

4. The compound of claim 1, wherein the mitochondrial targeting group MTG is $Ph_3P^+$.
5. The compound of claim 1, which comprises a cation selected from:
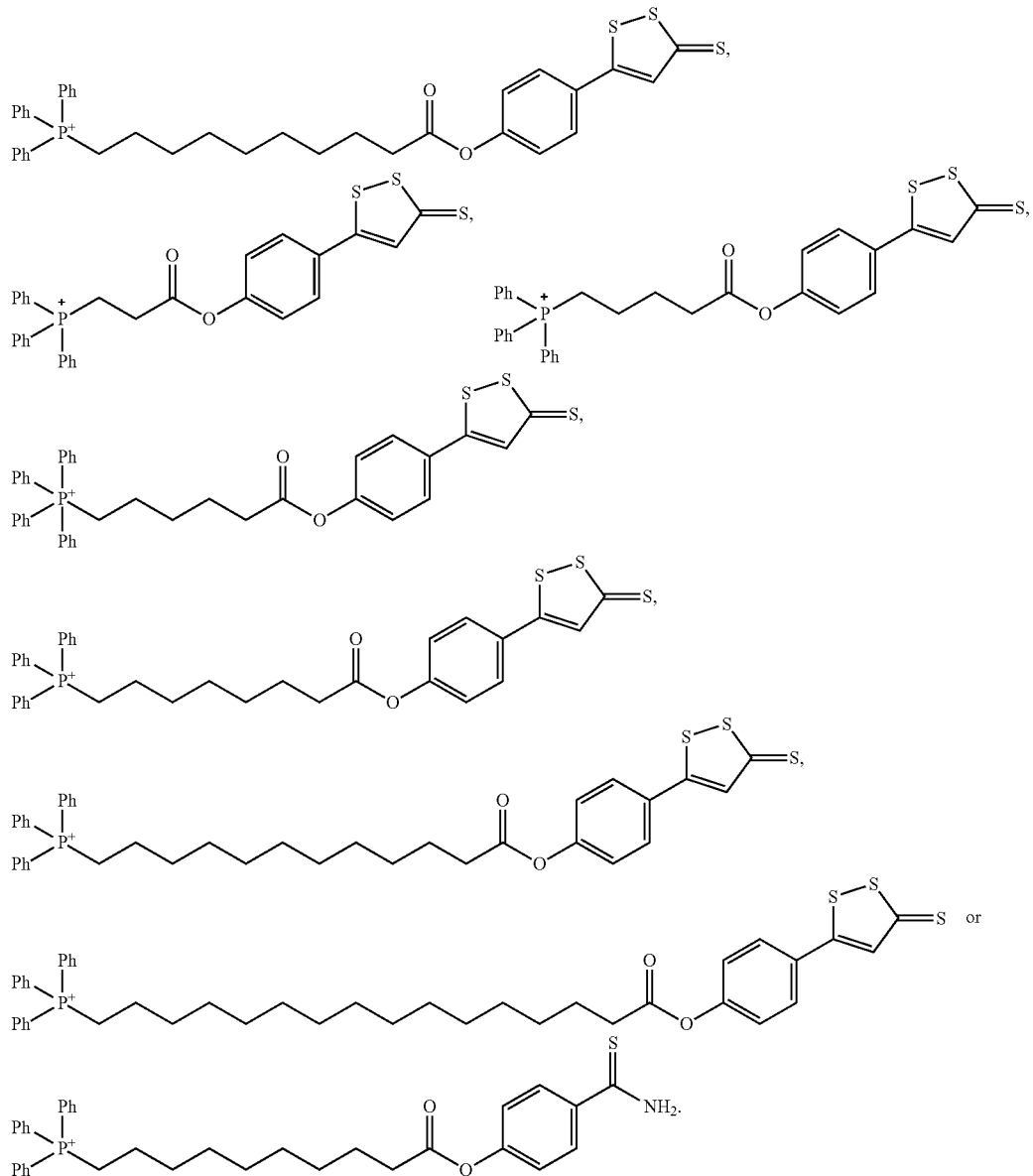
6. A pharmaceutical composition comprising the compound of claim 1 and a pharmaceutically acceptable excipient, diluent, or carrier.
* * * * *